(12) United States Patent
Suga

(10) Patent No.: US 6,241,656 B1
(45) Date of Patent: Jun. 5, 2001

(54) ENDOSCOPE SYSTEM HAVING SPATIAL FREQUENCY CONVERTER

(75) Inventor: Takeshi Suga, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/236,479

(22) Filed: Jan. 25, 1999

(30) Foreign Application Priority Data

Jan. 23, 1998 (JP) .................................................. 10-010954
Apr. 23, 1998 (JP) .................................................. 10-113056
Sep. 25, 1998 (JP) .................................................. 10-271687

(51) Int. Cl.$^7$ ....................................................... A61B 1/04
(52) U.S. Cl. ........................................... 600/109; 600/118
(58) Field of Search .................................. 600/109, 181, 600/117, 118; 348/65, 71, 72, 76

(56) References Cited

U.S. PATENT DOCUMENTS

| 4,827,908 | * | 5/1989 | Matsuo | 600/118 |
| 5,434,615 | * | 7/1995 | Matumoto | 348/72 |
| 5,868,666 | * | 2/1999 | Okada et al. | 600/118 |
| 5,951,462 | * | 9/1999 | Yamanaka | 600/118 |

FOREIGN PATENT DOCUMENTS

96/24085   8/1996   (WO) .

* cited by examiner

*Primary Examiner*—John P. Leubecker
(74) *Attorney, Agent, or Firm*—Pillsbury Winthrop LLP

(57) ABSTRACT

An endoscope system for observing an image of a subject on a monitor through a plurality of different types of endoscopes selectively connected thereto, which vary in the spatial frequency characteristics of their optical systems. At least one of the endoscopes has a spatial frequency characteristic converter in an optical system thereof. The endoscope system has a spatial frequency characteristic restoring device corresponding to the spatial frequency characteristics of an endoscope connected thereto and is therefore capable of enlarging the depth of field and producing a high-resolution image independently of the type of endoscope connected thereto.

14 Claims, 19 Drawing Sheets

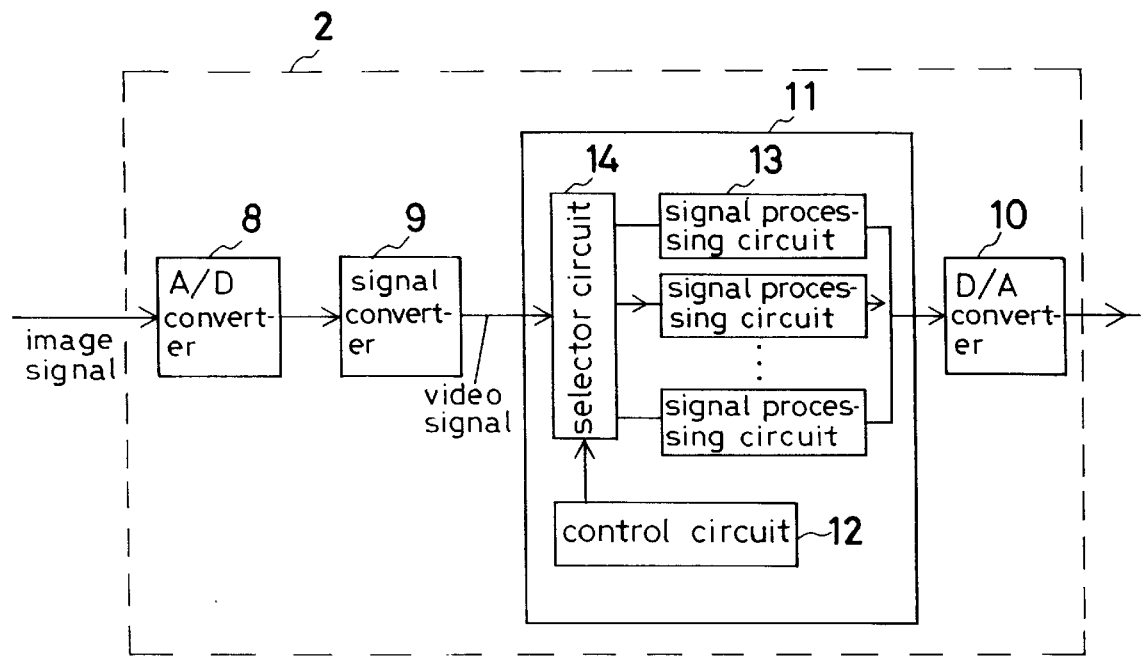
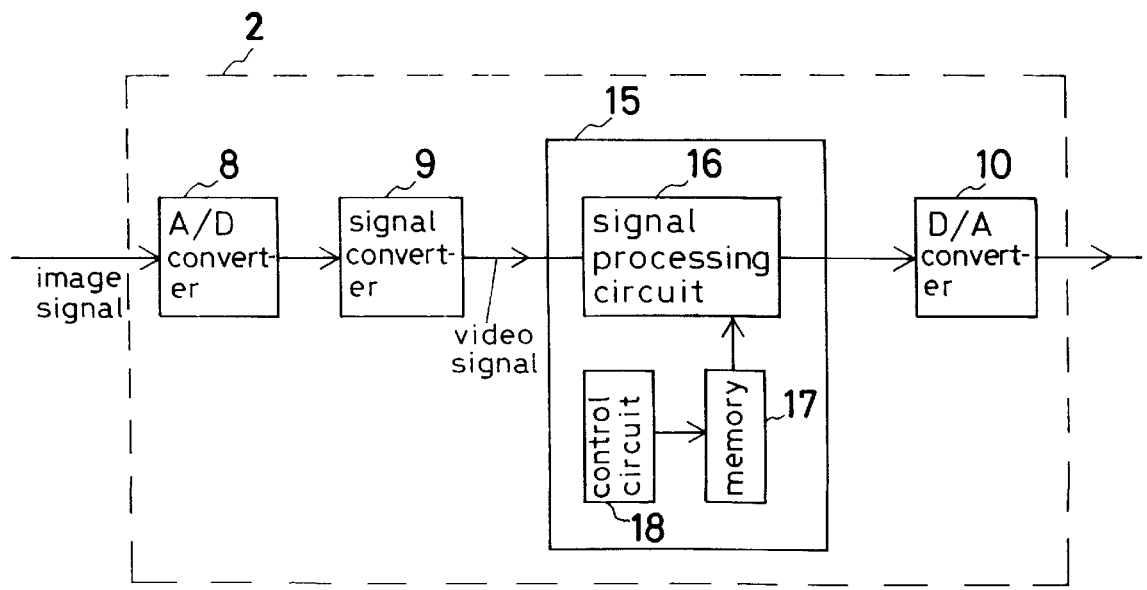

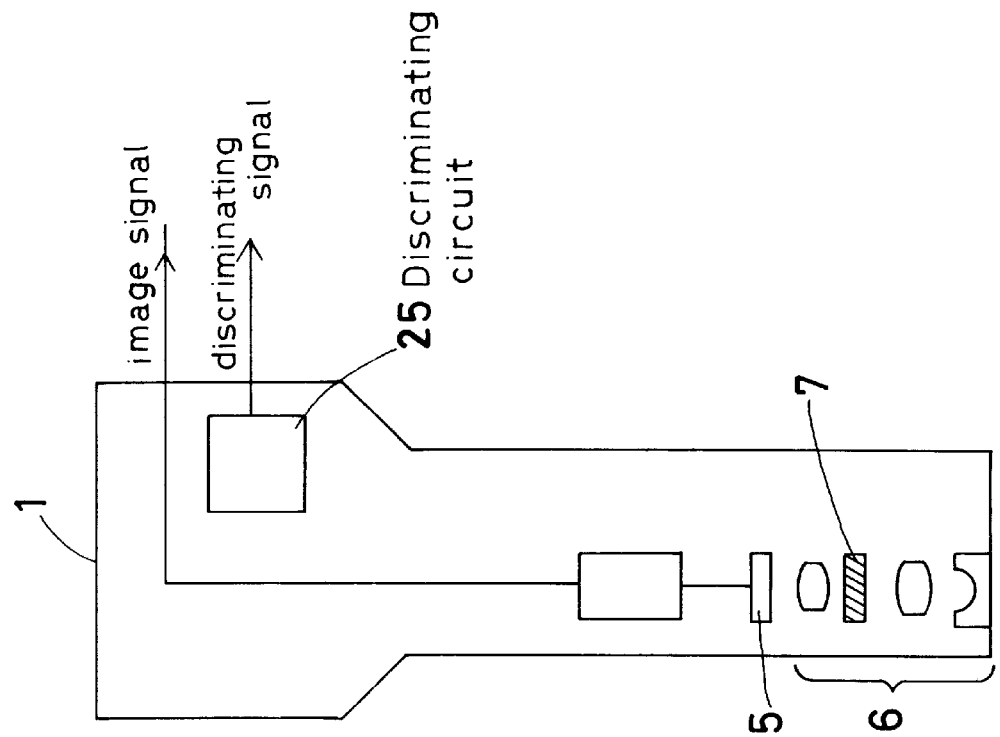
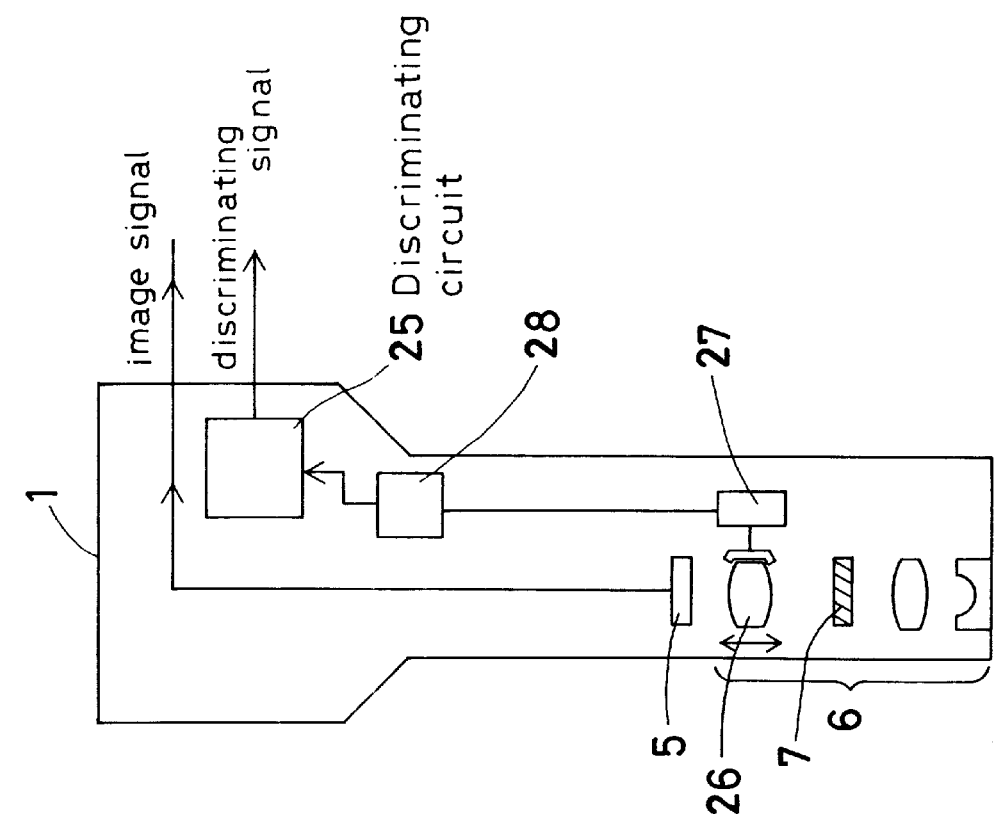

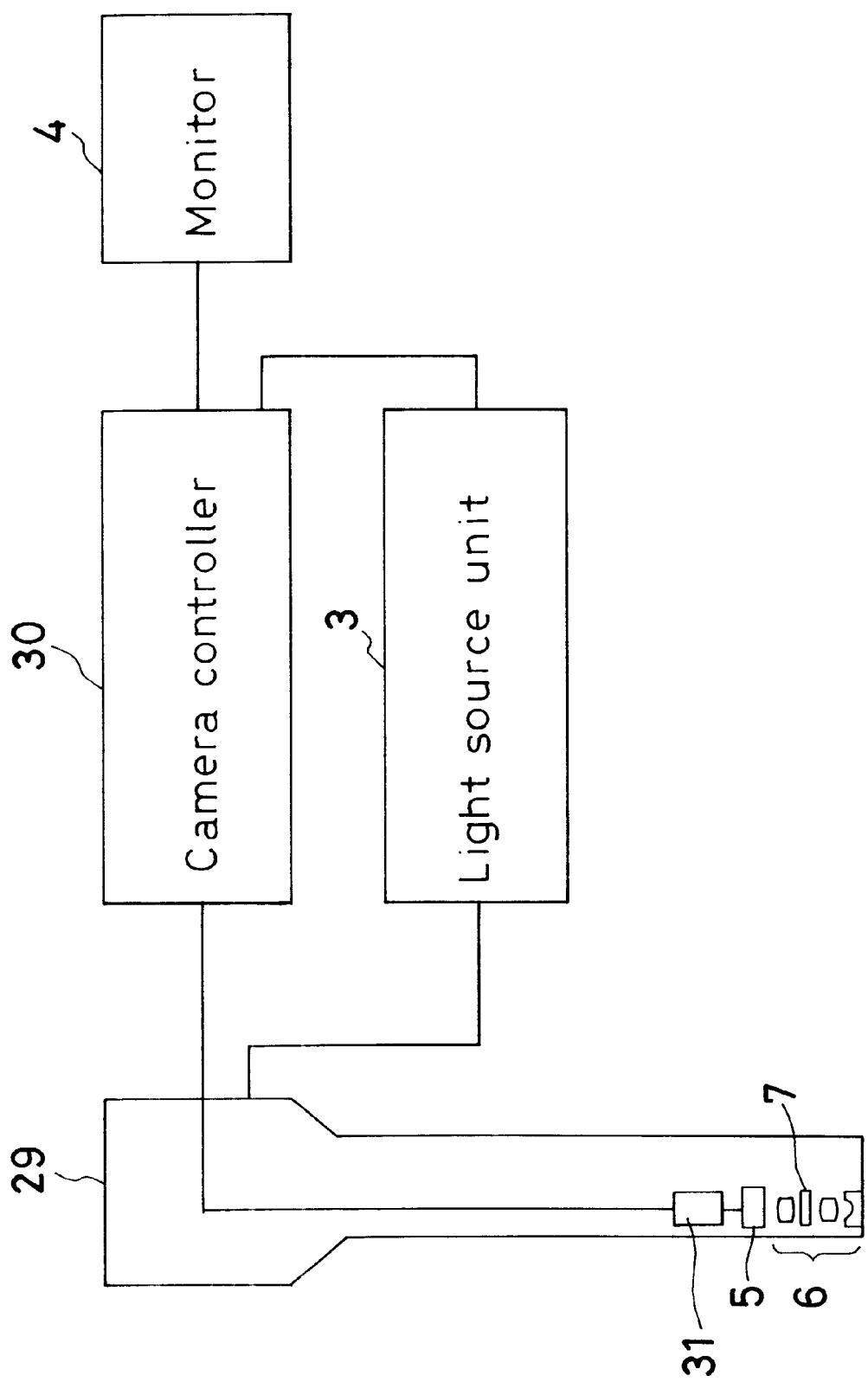

ENDOSCOPE SYSTEM HAVING SPATIAL FREQUENCY CONVERTER

BACKGROUND OF THE INVENTION

The present invention relates to an endoscope system and, more particularly, to an endoscope system for observing an image of a subject on a monitor through an endoscope selected from a plurality of different types of endoscopes.

As is well known, endoscopes enable observation of the inside of a living body or the like, which cannot directly be seen by visual observation, and are widely used for diagnostic and therapeutic purposes mainly in the field of medical treatments. In recent years, video endoscopes have become widespread in which a subject image is converted into electric signals by a solid-state image pickup device, e.g. a CCD, so as to be observable on a monitor.

A variety of such endoscopes are used according to parts or regions to be observed. In use, these endoscopes are selectively connected to a light source unit, a signal processing device, etc. Accordingly, a plurality of different types of signal processing circuits must be prepared for various endoscopes. Under these circumstances, Japanese Patent Application Unexamined Publication (KOKAI) No. 6-304135, for example, discloses an apparatus for converting image signals from different solid-state image pickup devices into a video signal displayable on a monitor.

FIG. 22 is a schematic diagram of a conventional camera controller (image processor) 2. An image signal from an endoscope 1 connected to the camera controller 2 is converted into a digital signal by an A/D converter 8 and then sent to a signal converter 9. In the signal converter 9, the image signal, which corresponds to the type of solid-state image pickup device 5 mounted in the connected endoscope 1, is converted into a video signal displayable on a monitor. The video signal from the signal converter 9 is converted into an analog signal by a D/A converter 10, and an image is displayed on the monitor.

Japanese Patent Application Unexamined Publication (KOKAI) No. 8-313823 discloses an endoscope image processing apparatus that processes a video signal obtained from a video endoscope. This type of apparatus performs image processing corresponding to the spatial frequency characteristics of an image of a subject that are expressed by the product of the spatial frequency characteristics of the subject and the spatial frequency characteristics of the associated optical system. The endoscope image processing apparatus mainly performs image processing such as edge enhancement to aid in human visual recognition, thereby improving diagnostic capability.

PCT/US96/01514 discloses a technique of converting the spatial frequency characteristics of an optical system by using a phase filter to enlarge the depth of field of the optical system. When a phase filter is used, the spatial frequency response of the optical system lowers in the frequency range from a high-frequency region to an intermediate-frequency region, and a phase shift is produced at each frequency. To solve these problems, PCT/US96/01514 is arranged to execute signal processing for increasing the spatial frequency response of the optical system in the frequency range of from a high-frequency region to an intermediate-frequency region and for correcting the phase shift at each frequency, thereby obtaining an image of high quality with an enlarged depth of field of the optical system.

FIG. 23 is a diagram schematically showing the arrangement of a conventional imaging system arranged to enlarge the depth of field as stated above. The conventional imaging system includes an imaging optical system 6, a spatial frequency characteristic converter 7, a solid-state image pickup device 5, a spatial frequency restoring device 11', and a monitor 4. In this case, an individual system is needed for each of the required characteristics of the system, i.e. depth of field, focal length, and F-number.

When a technique of enlarging the depth of field of an optical system, for example, by using a spatial frequency characteristic converting device, e.g. a phase filter, is applied to an endoscope, it is necessary to use a spatial frequency characteristic restoring device for restoring the degraded spatial frequency characteristics of the optical system to obtain an image of high resolution.

In this regard, the existing endoscope systems have only the function of converting image signals from various endoscopes having different solid-state image pickup devices into a video signal displayable on a monitor.

In the existing endoscope image processing apparatus, image processing corresponding to the spatial frequency characteristics of each individual image is carried out. That is, image processing changes according to the kind of subject. However, it is difficult to obtain the spatial frequency characteristics of the optical system from the spatial frequency characteristics of the image.

Accordingly, the existing endoscope systems and endoscope image processing apparatus have the problem that it is impossible to accurately restore the spatial frequency characteristics of the endoscope optical system degraded by a spatial frequency characteristic converting device and to thereby obtain an image of high resolution.

Furthermore, the required characteristics of the endoscope optical system, e.g. focal length, depth of field, and numerical aperture, are specified variously according to each particular use application. Accordingly, there is a need for an endoscope system to which a plurality of endoscopes can be selectively connected regardless of whether or not an endoscope to be connected has a spatial frequency characteristic converting device and irrespective of the type of spatial frequency characteristic converting device, and which can produce an image of high resolution.

However, PCT/US96/01514 is a system in which a spatial frequency characteristic converting device and a spatial frequency characteristic restoring device are in one-to-one correspondence to each other. Therefore, the system cannot use an endoscope having a different spatial frequency characteristic converting device or an endoscope having no spatial frequency characteristic converting device.

SUMMARY OF THE INVENTION

In view of the above-described circumstances of the prior art, an object of the present invention is to provide an endoscope system that allows a plurality of endoscopes varying in the spatial frequency characteristics of their optical systems to be selectively connected thereto and is capable of enlarging the depth of field and producing an image of high resolution independently of the type of endoscope connected thereto.

To attain the above-described object and others, the present invention provides an endoscope system for observing an image of a subject on a monitor through a plurality of different types of endoscopes selectively connected to the endoscope system. At least one of the endoscopes has a spatial frequency characteristic converting device in an optical system thereof. The endoscope system has a spatial frequency characteristic restoring device corresponding to the spatial frequency characteristics of an endoscope connected to the endoscope system.

In this case, it is desirable that the spatial frequency characteristic restoring device should vary according to whether or not the endoscope connected to the endoscope system has a spatial frequency characteristic converting device.

It is also desirable that the spatial frequency characteristic restoring device should be determined from measured values of the spatial frequency characteristics of an optical system of the endoscope connected to the endoscope system.

The spatial frequency characteristic restoring device may be provided in a camera controller (image processor). Alternatively, the spatial frequency characteristic restoring device may be provided in the endoscope connected to the endoscope system.

As the spatial frequency characteristic converting device, a pupil modulation element may be used.

The endoscope may have an objective optical system for forming a subject image and a solid-state image pickup device for detecting the image formed by the objective optical system. Alternatively, the endoscope may be a hard endoscope including an objective optical system for forming a subject image, an image transfer optical system, and an ocular optical system. In this case, the endoscope system has an adapter for forming the subject image from the hard endoscope on a solid-state image pickup device.

In the latter case, it is desirable that the spatial frequency characteristic converting device should be provided in an optical system of the adapter. In this case, it is desirable that the spatial frequency characteristic restoring device should correspond to the exit pupil diameter of the hard endoscope connected to the endoscope system.

It is also desirable that when an endoscope having an optical system whose spatial frequency characteristics are variable is connected to the endoscope system, the spatial frequency characteristic restoring device should be switched to another according to a change in the spatial frequency characteristics of the optical system.

In this case, the optical system may be a variable-focus optical system. It is desirable that the spatial frequency characteristic restoring device should be switched to another according to a change in the focal length of the variable-focus optical system.

The endoscope system according to the present invention has a spatial frequency characteristic restoring device corresponding to the spatial frequency characteristics of an endoscope connected thereto. Therefore, it is possible to enlarge the depth of field and to produce an image of high resolution for any type of endoscope irrespective of whether or not the connected endoscope has a spatial frequency characteristic converting device and regardless of the type of spatial frequency characteristic converting device.

In a case where the spatial frequency characteristic restoring device for restoring the degraded characteristics varies according to whether or not the endoscope connected to the endoscope system has a spatial frequency characteristic converting device, it is possible to simplify the arrangement of the spatial frequency characteristic restoring device and to reduce the cost thereof by arranging the system, for example, such that when an endoscope having a spatial frequency characteristic converting device is connected, the spatial frequency characteristic restoring device is used, whereas when a conventional endoscope having no spatial frequency characteristic converting device is connected, restoration of the spatial frequency characteristics is not carried out.

In a case where the spatial frequency characteristic restoring device is determined from measured values of the spatial frequency characteristics of the endoscope optical system, it is possible to minimize for each endoscope the effect of manufacturing errors introduced by processing and assembly of the optical system, including the spatial frequency characteristic converting device. Accordingly, it is possible to minimize the lowering of the resolution of images due to manufacturing errors. In addition, minimization of the effect of manufacturing errors makes it possible to increase the yield during the production phase and to realize a reduction in cost.

In a case where the spatial frequency characteristic converting device is provided in the endoscope, it is possible to provide both the spatial frequency characteristic converting device and the spatial frequency characteristic restoring device in the endoscope. Therefore, even when the endoscope is connected to a conventional camera controller (image processor) having no spatial frequency characteristic restoring device, it is possible to enlarge the depth of field and to produce an image of high resolution.

Even when the endoscope is connected to a camera controller having a spatial frequency characteristic restoring device, it is possible to enlarge the depth of field and to produce an image of high resolution by setting the system such that restoration of spatial frequency characteristics is not performed on the camera controller side.

Thus, the endoscope system is favorably compatible.

Furthermore, because each particular endoscope has a spatial frequency restoring device, it is possible to minimize for each endoscope the effect of manufacturing errors introduced by processing and assembly of the optical system, including the spatial frequency characteristic converting device. In other words, it becomes possible to determine a spatial frequency characteristic restoring device in view of the effect of manufacturing errors of the optical system in each endoscope. Accordingly, it is possible to increase the yield during the production phase of the optical system and to realize a reduction in the cost.

Furthermore, because the endoscope has a spatial frequency characteristic restoring device therein, it is possible to shorten the length of an electric cable for sending an image signal from the solid-state image pickup device to the spatial frequency characteristic restoring device. Consequently, it is possible to minimize an electric noise generated in the electric cable and hence possible to avoid degradation of the image quality, which might otherwise be caused by an electric noise generated in the electric cable and amplified by the spatial frequency characteristic restoring device.

If a pupil modulation element is used as the spatial frequency characteristic converting device, the spatial frequency characteristics of the optical system can be controlled directly.

In an endoscope system used by connecting an adapter to one of a plurality of different types of hard endoscopes each including an objective optical system for forming a subject image, an image transfer optical system, and an ocular optical system, the spatial frequency characteristic converting device is placed in the optical system of the adapter. By doing so, the hard endoscope can also be used with an eyepiece as in the conventional endoscope systems. The endoscope system can also be used as a conventional system by replacing the adapter with a conventional adapter having no spatial frequency characteristic converting device.

Furthermore, the depth of field of each of several different types of hard endoscopes can be enlarged with a single spatial frequency characteristic converting device by providing a spatial frequency characteristic restoring device corresponding to the exit pupil diameter of a hard endoscope connected to the adapter.

It is desirable that when an endoscope having an optical system whose spatial frequency characteristics are variable is connected to the endoscope system, the spatial frequency characteristic restoring device is switched to another according to a change in the spatial frequency characteristics. With this arrangement, it is possible to enlarge the depth of field and to produce an image of high resolution even in the case of an endoscope whose spatial frequency characteristics are variable.

When the spatial frequency characteristic converting device is applied to a variable-focus optical system, for example, the spatial frequency characteristics of the optical system change with the change in the focal length of the optical system, and the amount of conversion effected by the spatial frequency characteristic converting device also changes. Therefore, the focal length of the optical system is obtained from the lens drive quantity of the like, and the spatial frequency characteristic restoring device is switched to another on based on the focal length. By doing so, it is possible to enlarge the depth of field and to produce an image of high resolution even in a variable-focus optical system.

Still other objects and advantages of the invention will in part be obvious and will in part be apparent from the specification.

The invention accordingly comprises the features of construction, combinations of elements, and arrangement of parts which will be exemplified in the construction hereinafter set forth, and the scope of the invention will be indicated in the claims.

BRIEF DESCRIPTION OF THE DRAWINGS

FIG. 2 is a block diagram showing the arrangement of a first example of a camera controller used in the present invention.

FIG. 3 is a block diagram showing the arrangement of a second example of the camera controller in the present invention.

FIG. 4 is a diagram schematically showing a first example of an endoscope used in the present invention, which is provided with an electric circuit that generates a discriminating signal unique to the endoscope.

FIG. 5 is a diagram schematically showing a second example of an endoscope used in the present invention, which is provided with an electric circuit that generates a discriminating signal unique to the endoscope.

FIG. 6 is a diagram schematically showing the arrangement of a second embodiment of the endoscope system according to the present invention.

DESCRIPTION OF THE PREFERRED EMBODIMENTS

Embodiments of the endoscope system according to the present invention will be described below with reference to the accompanying drawings.

Figure 1:
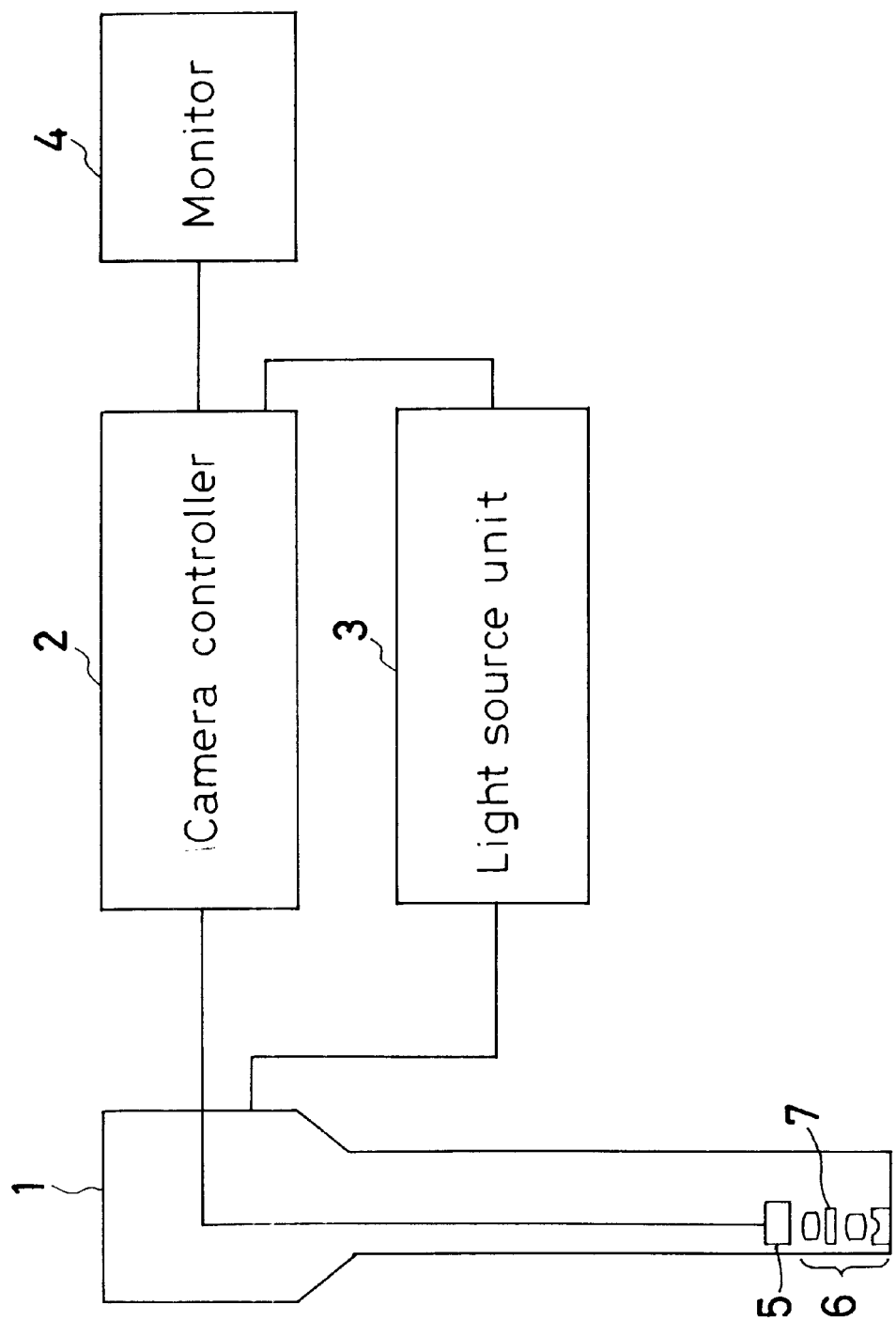
FIG. 1 is a diagram schematically showing a first embodiment of the endoscope system according to the present invention.

FIG. 1 is a diagram schematically showing the arrangement of a first embodiment of the endoscope system according to the present invention.

As shown in FIG. 1, the endoscope system includes an endoscope 1 having a solid-state image pickup device 5 and an imaging optical system 6 that forms an image of a subject on the solid-state image pickup device 5. A camera controller (image processor) 2 processes an image signal obtained with the endoscope 1 to output a video signal. A monitor 4 displays the video signal from the camera controller 2. A light source unit 3 generates illuminating light for observation.

The endoscope system according to the present invention is arranged so that a plurality of different types of endoscopes 1 can be selectively connected thereto. At least one of the plurality of different types of endoscopes 1 has a spatial frequency characteristic converter 7, such as a pupil modulation element, provided in the imaging optical system 6.

The camera controller 2 has a spatial frequency characteristic restoring device corresponding to the spatial frequency characteristics of the endoscope 1 connected to the endoscope system to perform spatial frequency characteristic restoring processing on an image signal obtained with the endoscope 1.

Thus, according to this embodiment, a plurality of endoscopes 1 varying in the spatial frequency characteristics of their optical system can be selectively connected to a single camera controller 2. In addition, the endoscope 1 connected to the camera controller 2 can enlarge the depth of field and produce an image of high resolution. It is also possible to simplify the arrangement of the endoscope system and to reduce the cost thereof.

FIG. 2 is a block diagram showing the arrangement of a first example of the camera controller 2 used in the present invention. An image signal from an endoscope 1 connected to the camera controller 2 is converted into a digital signal by an A/D converter 8 and then sent to a signal converter 9. The signal converter 9 converts the image signal, which corresponds to the type of solid-state image pickup device 5 mounted in the connected endoscope 1, into a video signal and sends it to a spatial frequency restoring unit 11.

The spatial frequency restoring unit 11 has a control circuit 12, a plurality of signal processing circuits 13 that execute filtering processing to restore spatial frequency characteristics, and a selector circuit 14 that makes selection to send the video signal to a specific signal processing circuit 13.

The type of endoscope 1 connected to the camera controller 2 is discriminated by a discriminating signal that is input by the user through an input device (not shown) provided in connection with the camera controller 2. When a discriminating signal corresponding to the type of connected endoscope 1 is sent to the control circuit 12, the control circuit 12 sends a selection signal corresponding to the discriminating signal to the selector circuit 14. The selector circuit 14 selects a specific signal processing circuit 13 from among a plurality of signal processing circuits 13. It should be noted that the type of connected endoscope 1 can also be discriminated by a signal from an electric circuit provided in each particular endoscope 1 to generate a discriminating signal unique to the endoscope 1.

FIG. 4 is a diagram schematically showing the arrangement of a first example of an endoscope 1 provided with an electric circuit generating a discriminating signal unique to the endoscope 1. This is an example of an endoscope 1 having a fixed-focus imaging optical system 6.

The endoscope 1 includes a solid-state image pickup device 5 and a fixed-focus imaging optical system 6 that forms an image of a subject on the solid-state image pickup device 5. The endoscope 1 further includes a spatial frequency characteristic converter 7 and a discriminating circuit 25 that generates a signal discriminating the type of endoscope 1. Information concerning the subject image is converted into an image signal by the solid-state image pickup device 5 and transferred to the camera controller 2. The signal discriminating the type of endoscope 1 is transferred from the discriminating circuit 25 to the camera controller 2. Thus, the endoscope of this example has the discriminating circuit 25 for generating a signal discriminating the type of endoscope 1 and hence enables a proper spatial frequency characteristic restoring device to be automatically selected on the basis of the discriminating signal.

FIG. 5 is a diagram schematically showing the arrangement of a second example of an endoscope 1 provided with an electric circuit that generates a discriminating signal unique to the endoscope 1 as stated above. This is an example of an endoscope 1 having a variable-focus optical system 6.

In the variable-focus optical system 6, as the focal length changes, the spatial frequency characteristics also change. Accordingly, the amount of conversion effected by the spatial frequency characteristic converter 7 also changes. Therefore, it is necessary to change spatial frequency characteristic restoring devices from one to another according to the amount of change in the focal length.

When the user drives a lens-driving device 27 through an input device (not shown), a movable lens 26 in the optical system 6 is moved along an optical axis, thereby changing the focal length of the optical system 6. The lens-driving device 27 may adopt driving by a piezoelectric element or driving by a wire. A signal corresponding to the lens drive quantity is sent from the lens-driving device 27 to a computing circuit 28. The computing circuit 28 obtains a focal length of the optical system 6 from the lens drive quantity for the lens 26 and sends a signal corresponding to the focal length obtained to the discriminating circuit 25.

The discriminating circuit 25 delivers a selection signal to select a spatial frequency characteristic restoring device corresponding to the focal length of the optical system 6. Spatial frequency characteristic restoring devices are switched from one to another on the basis of the selection signal, thereby making it possible to enlarge the depth of field and to produce an image of high quality even in the case of the variable-focus optical system 6.

It should be noted that spatial frequency characteristic restoring devices corresponding to various focal lengths may be previously determined by simulation or the like.

Referring to FIG. 2, the selector circuit 14 selects one signal processing circuit 13 and transfers the video signal to the selected signal processing circuit 13. When an endoscope 1 having a spatial frequency characteristic converter 7 is connected to the camera controller 2, a signal processing circuit 13 is selected which has an inverse frequency characteristic filter corresponding to the spatial frequency characteristics of the imaging optical system 6 in each of the R (red), G (green) and B (blue) wavelength regions, or which has a digital filter equivalent to it, thereby executing filter processing for restoring the spatial frequency characteristics in each of the R, G and B wavelength regions. Filters used herein to restore the spatial frequency characteristics may be prepared, for example, on the basis of the result of calculation performed by a simulation on the spatial frequency characteristics of imaging optical systems 6 to be used and associated pupil modulation elements.

The plurality of signal processing circuits 13 include a conventional signal processing circuit executing image processing and a conventional signal processing circuit that does not perform image processing. Therefore, when an endoscope 1 that does not have a spatial frequency characteristic converter is connected to the camera controller 2, such a conventional signal processing circuit is selected so as not to execute filter processing for restoring spatial frequency characteristics.

The video signal from the spatial frequency restoring unit 11 is converted into an analog signal by a D/A converter 10, and a restored image is displayed on the monitor 4.

According to this example, the spatial frequency restoring unit 11, which is a spatial frequency characteristic restoring device, is provided with a plurality of signal processing circuits 13 capable of executing filter processing for restoring spatial frequency characteristics corresponding to various spatial frequency characteristic converters 7. Therefore, it is possible to enlarge the depth of field and to produce an image of high resolution for any type of endoscope connected to the camera controller 2. In addition, it is possible to simplify the arrangement of the endoscope system and to reduce the cost thereof.

FIG. 3 is a block diagram showing the arrangement of a second example of the camera controller 2 used in the present invention. An image signal from an endoscope 1 connected to the camera controller 2 is converted into a digital signal by the A/D converter 8, and the digital signal is sent to the signal converter 9. In the signal converter 9, the image signal, which corresponds to the type of solid-state image pickup device 5 mounted in the connected endoscope 1, is converted into a video signal, and the video signal is sent to a spatial frequency restoring unit 15.

The spatial frequency restoring unit 15 includes a signal processing circuit 16 formed from a programmable logical element, a memory 17, and a control circuit 18.

The memory 17 contains program data (equation and numerical values) concerning an inverse frequency characteristic filter, or a digital filter equivalent to it, corresponding to the spatial frequency characteristics in each of the R, G and B wavelength regions of the imaging optical system 6 of each of endoscopes 1 that may be connected to the endoscope system.

As has been stated in connection with the first example, a discriminating signal that discriminates the type of connected endoscope 1 is sent to the control circuit 18. In response to a signal from the control circuit 18, data concerning a filter corresponding to the spatial frequency characteristics of the connected endoscope 1 is transferred from the memory 17 to the signal processing circuit 16 to execute filter processing for restoring the spatial frequency characteristics in each of the R, G and B wavelength regions. The video signal from the spatial frequency restoring unit 15 is converted into an analog signal by the D/A converter 10, and a restored image is displayed on the monitor 4.

According to this example, the circuitry scale can be reduced because the camera controller 2 uses a signal processing circuit 16 formed from a programmable logical element. Because spatial frequency restoring filters can be changed by changing programs, expandability is favorably high.

Restoration of spatial frequency characteristics may be performed also when an endoscope 1 having no spatial frequency characteristic converter is connected to the camera controller 2. By doing so, it becomes unnecessary to raise the spatial frequency characteristics of the imaging optical system 6 in the endoscope 1, and it is possible to realize a reduction in the number of constituent lens elements of the optical system 6 and also a reduction in the lens length.

The arrangement may be such that the spatial frequency characteristics of the imaging optical system 6 in each endoscope 1 to be connected to the camera controller 2 are measured, and a program corresponding to the required spatial frequency characteristic restoring filters is prepared from the measured values. The spatial frequency characteristics of the imaging optical system 6 can be measured by imaging a sufficiently small point source of light and Fourier-transforming the obtained point source image by image processing.

Thus, it is possible to minimize for each endoscope 1 the effect of manufacturing errors introduced by processing and assembly of the optical system 6, including the spatial frequency characteristic converter 7. Accordingly, it is possible to minimize the lowering in the resolution of images due to manufacturing errors. In addition, minimization of the effect of manufacturing errors makes it possible to increase the yield during the production phase and to realize a reduction in the cost.

FIG. 6 is a diagram schematically showing the arrangement of a second embodiment of the endoscope system according to the present invention.

As shown in FIG. 6, the endoscope system includes an endoscope 29 having a solid-state image pickup device 5 and an imaging optical system 6 that forms an image of a subject on the solid-state image pickup device 5. A camera controller 30 processes an image signal obtained with the endoscope 29 to output a video signal. A monitor 4 displays the video signal from the camera controller 30. A light source unit 3 generates illuminating light for observation.

The endoscope system according to the present invention is arranged so that a plurality of different types of endoscopes 29 can be selectively connected thereto. At least one of the plurality of different types of endoscopes 29 has a spatial frequency characteristic converter 7, such as a pupil modulation element, provided in the imaging optical system 6. The endoscope 29 is provided therein with a spatial frequency restoring circuit 31 that performs restoration of spatial frequency characteristics corresponding to the spatial frequency characteristic converter 7.

Figure 22:
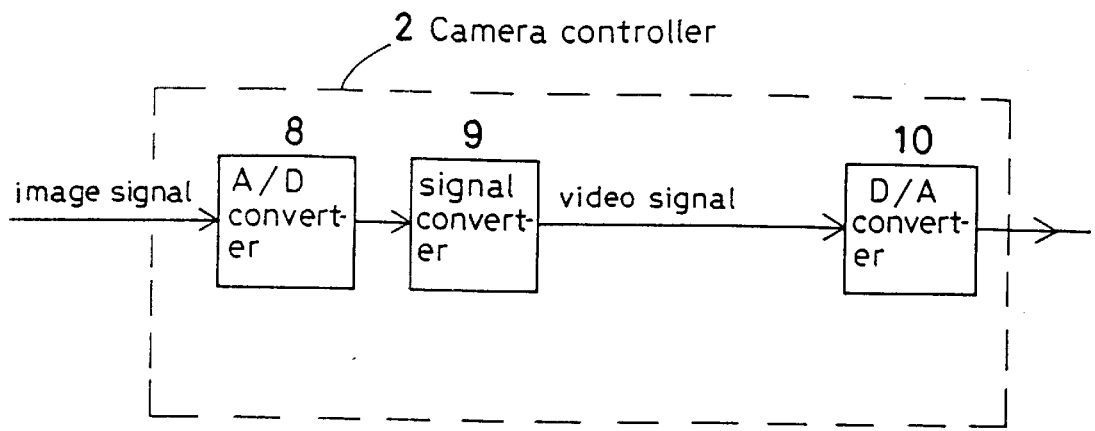
FIG. 22 is a schematic diagram of a conventional camera controller (image processor).
Figure 23:
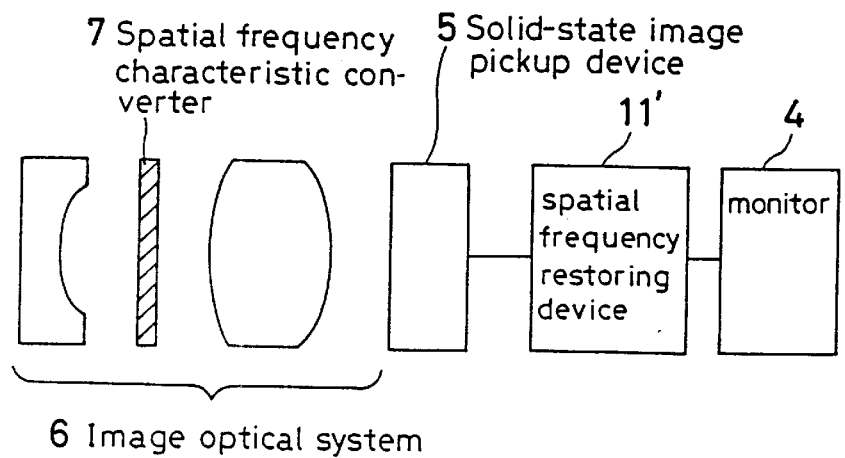
FIG. 23 is a diagram schematically showing the arrangement of a conventional imaging system arranged to enlarge the depth of field.

The camera controller 30 may be a conventional camera controller having no spatial frequency characteristic restoring device. The circuit configuration of the conventional camera controller may be such as that shown in FIG. 22.

Figure 7:
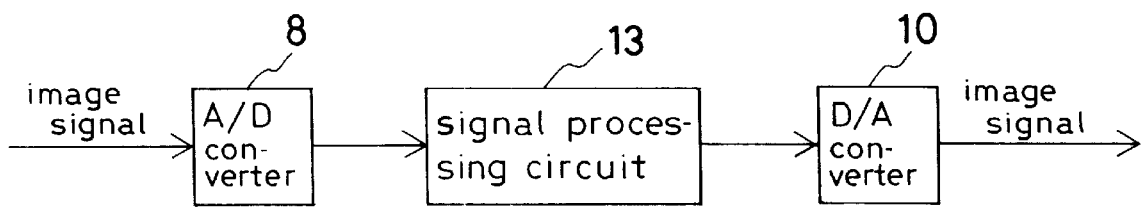
FIG. 7 is a block diagram showing the arrangement of an example of a spatial frequency restoring circuit.

An example of the spatial frequency restoring circuit 31 is shown in FIG. 7. An image signal from the solid-state image pickup device 5 is converted into a digital signal by an A/D converter 8 and then sent to a signal processing circuit 13. The signal processing circuit 13 executes filter processing in each of the R, G and B wavelength regions by using an inverse frequency characteristic filter corresponding to the spatial frequency characteristics of the imaging optical system 6 in each of the R, G and B wavelength regions or a digital filter equivalent to it. The image signal from the signal processing circuit 13 is converted into an analog signal by a D/A converter 10, and the analog signal is transferred to the camera controller 30. In the camera controller 30, the image signal from the spatial frequency restoring circuit 31 is converted into a video signal and then transferred to the monitor 4. The monitor 4 displays an image with an enlarged depth of field.

Thus, in this embodiment, each particular endoscope 29, which has a spatial frequency characteristic converter 7, has a spatial frequency restoring circuit 31.

Even when an endoscope 29 is connected to a conventional camera controller having no spatial frequency characteristic restoring device, it is possible to enlarge the depth of field and to produce an image of high resolution. Accordingly, the endoscope system is favorably compatible.

In addition, because each particular endoscope 29 has a spatial frequency restoring circuit 31, it is possible to minimize for each endoscope 29 the effect of manufacturing errors introduced by processing and assembly of the optical system 6, including the spatial frequency characteristic converter 7. In other words, it becomes possible to determine a spatial frequency characteristic restoring device in view of the effect of manufacturing errors of the optical system 6 in each endoscope 29. Accordingly, it is possible to increase the yield during the production phase of the optical system 6 and to realize a reduction in the cost. For example, inverse frequency characteristic filters may be determined on the basis of values obtained by measuring the spatial frequency characteristics of the optical system 6.

Furthermore, because the endoscope 29 has a spatial frequency characteristic restoring device therein, it is possible to shorten the length of an electric cable for sending an image signal from the solid-state image pickup device 5 to the spatial frequency restoring circuit 31, which is a spatial frequency characteristic restoring device. Consequently, it is possible to minimize an electric noise generated in the electric cable and hence possible to avoid degradation of the image quality, which might otherwise be caused by an electric noise generated in the electric cable and amplified by the spatial frequency characteristic restoring device. Incidentally, if the spatial frequency restoring circuit 31 and the solid-state image pickup device 5 are integrally fabricated by using a device such as a CMOS, the electric noise can be further reduced.

The endoscope 29 may be connected to a camera controller 2 having a spatial frequency characteristic restoring device (see FIG. 1). In this case, the system is set such that restoration of spatial frequency characteristics is not performed on the camera controller side. Thus, it is possible to enlarge the depth of field and to produce an image of high resolution.

In a case where the imaging optical system 6 is a variable-focus optical system, the spatial frequency restoring circuit 31 should be arranged to have a plurality of spatial frequency characteristic restoring devices as shown in FIGS. 2 and 3. With this circuit configuration, the spatial frequency characteristic restoring devices are switched from one to another according as the focal length of the optical system 6 changes.

Figure 8:
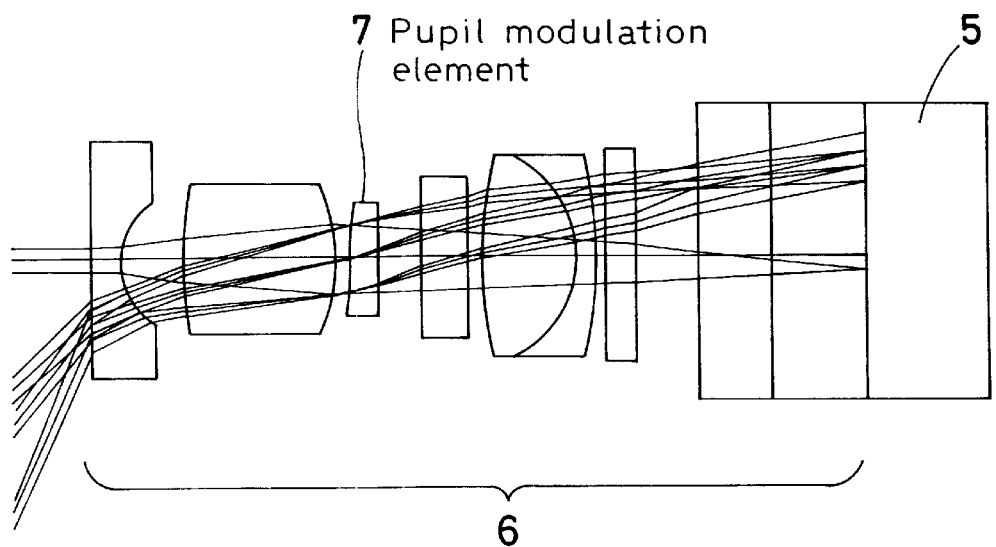
FIG. 8 is a sectional view of one example of an imaging optical system.

FIG. 8 shows one example of the imaging optical system 6. FIG. 8 is a sectional view of a solid-state image pickup device 5 and an imaging optical system 6 of an endoscope, which is an objective optical system for forming a subject image on the solid-state image pickup device 5. The imaging optical system 6 shown in FIG. 8 has a pupil modulation element 7 placed at the position of an aperture stop. The aperture stop configuration is a square aperture, each side of which is 0.92 millimeters long. The pupil modulation element 7 uses a free-form surface having a configuration expressed by $0.15(x^3+y^3)$. The refractive index of the pupil modulation element 7 is 1.52. It should be noted that the optical axis of the optical system 6 is defined as a z-axis, and coordinate axes perpendicularly intersecting the z-axis are defined as x- and y-axes, respectively. Lengths are given in millimeters.

The pupil modulation element 7 performs phase modulation of $\exp\{i26\pi(x^3+y^3)/0.46^3\}$ on parallel rays of light of wavelength 587.6 nanometers.

Figure 9:
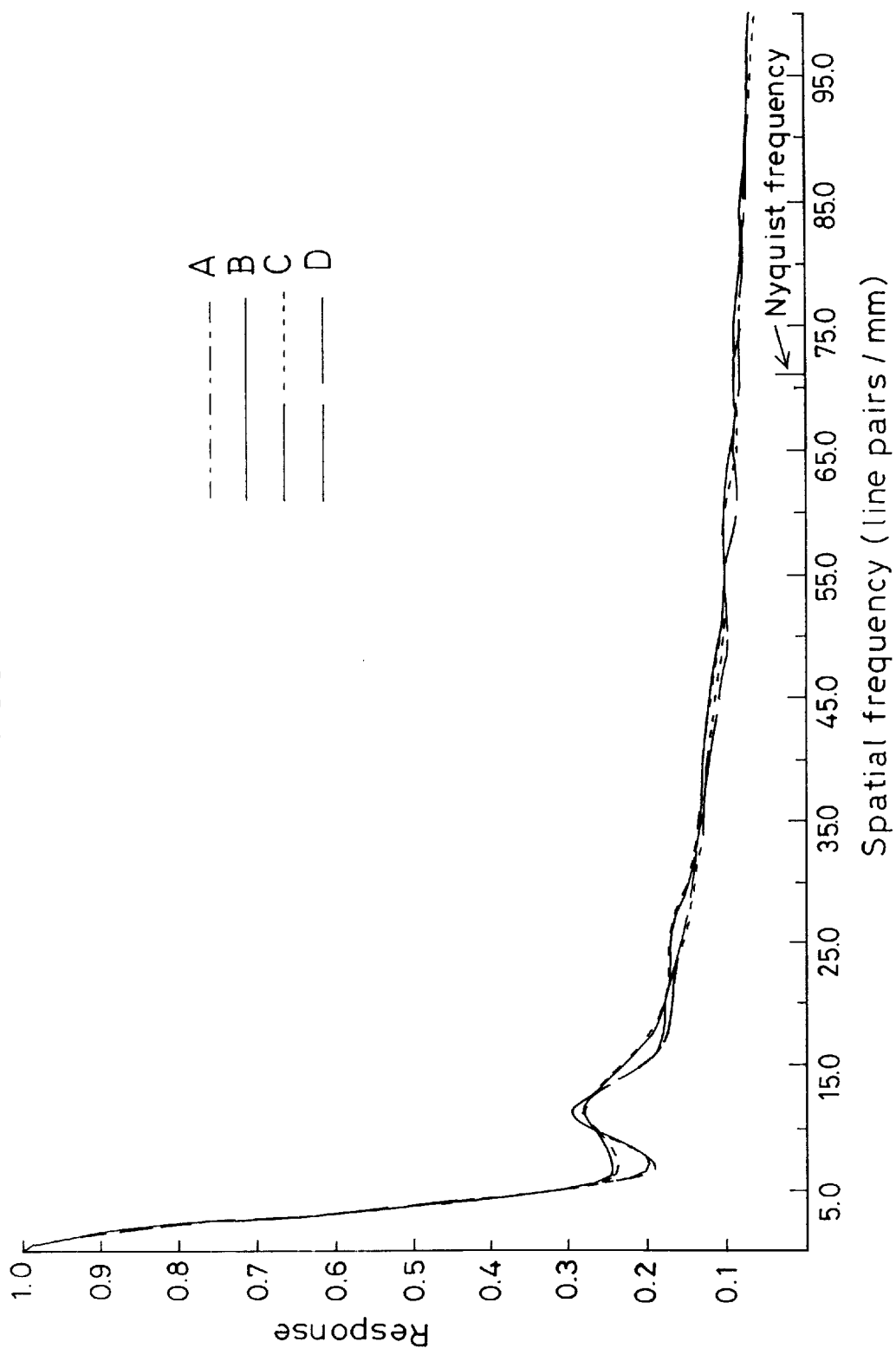
FIG. 9 is a diagram showing the spatial frequency response of the imaging optical system shown in FIG. 8 in a case where the distance to a subject is 100 millimeters.
Figure 10:
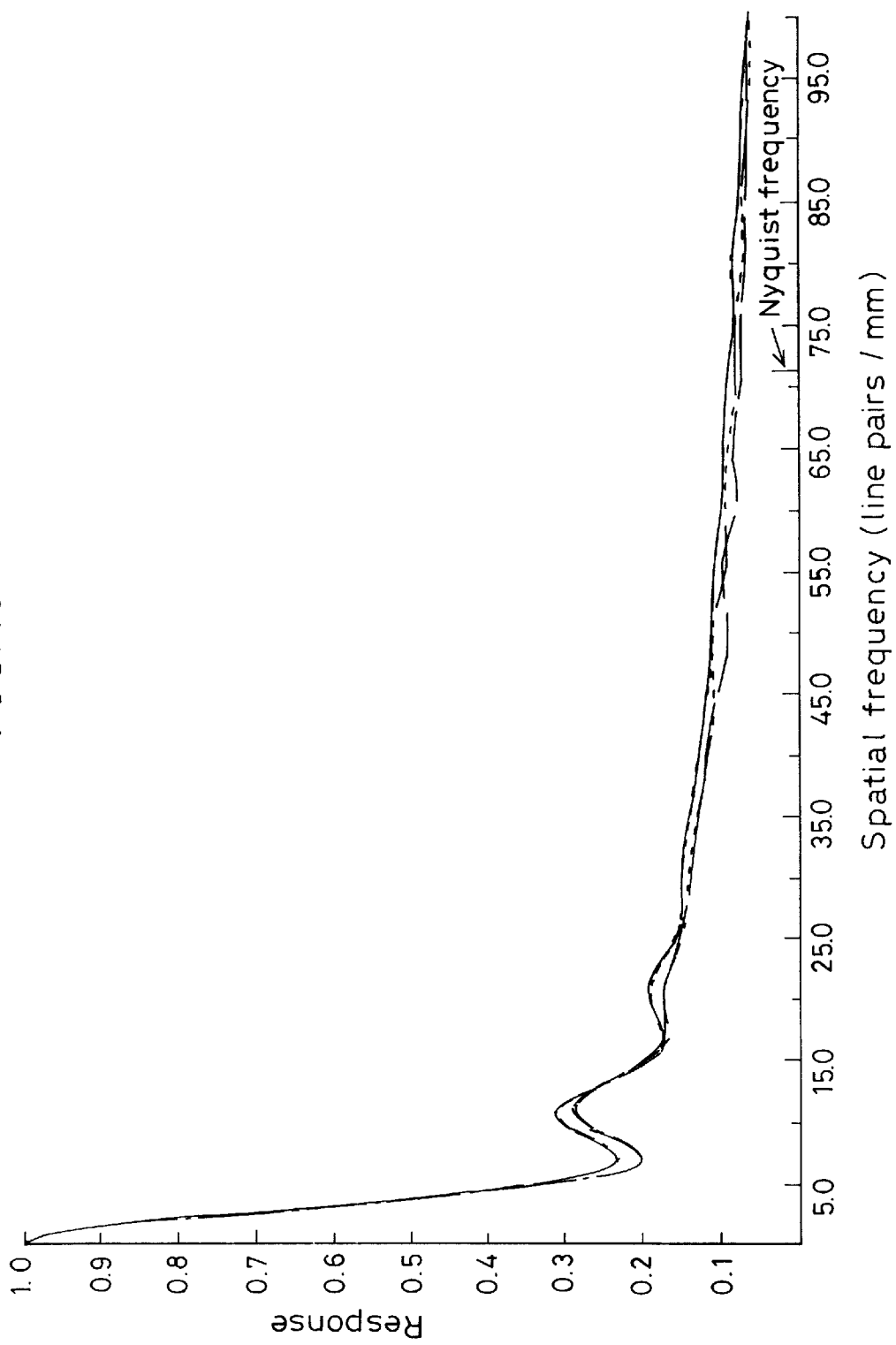
FIG. 10 is a diagram showing the spatial frequency response of the imaging optical system shown in FIG. 8 in a case where the subject distance is 13.5 millimeters.
Figure 11:
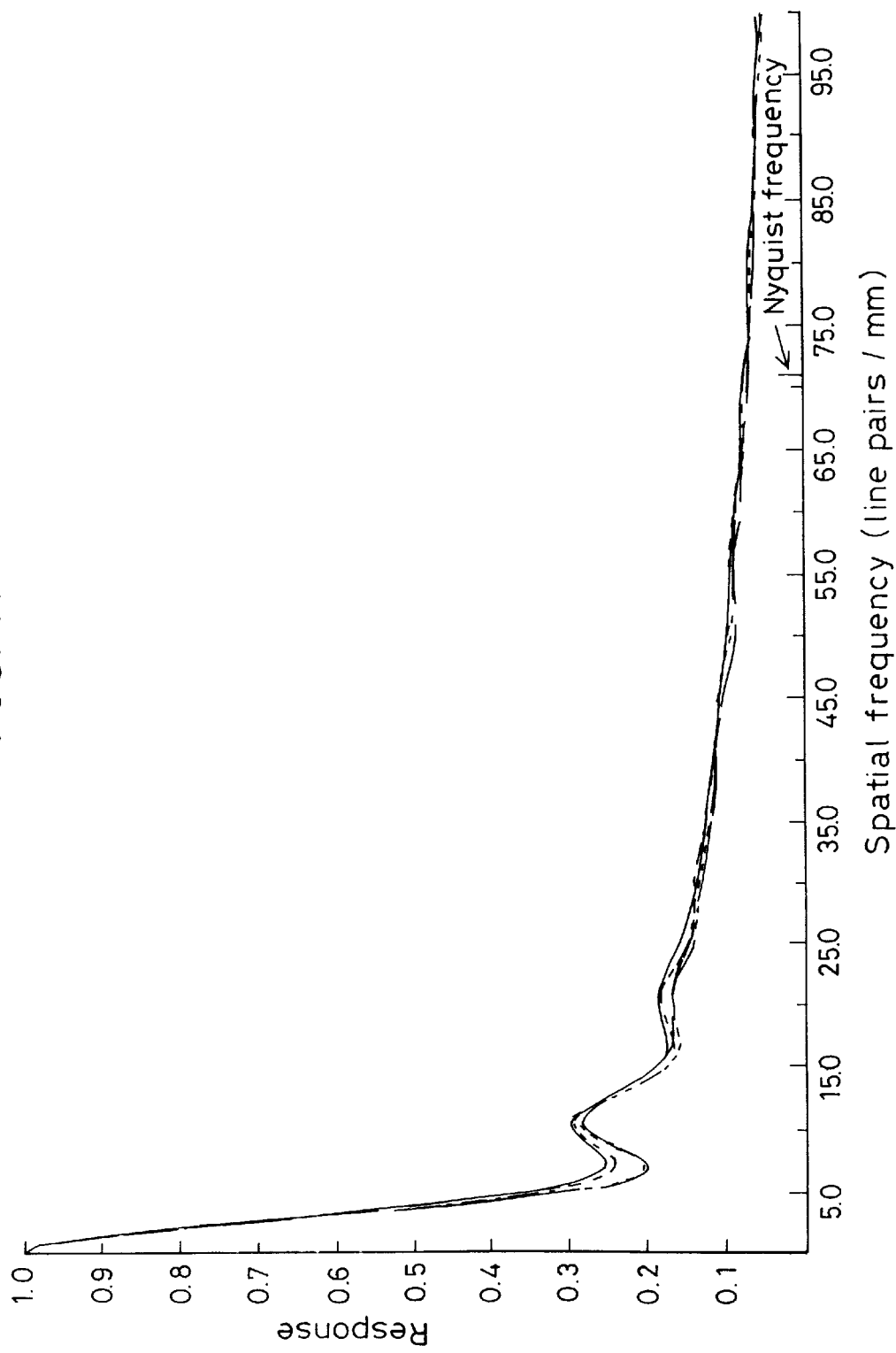
FIG. 11 is a diagram showing the spatial frequency response of the imaging optical system shown in FIG. 8 in a case where the subject distance is 5 millimeters.

FIGS. 9 to 11 show the results of calculation of the spatial frequency characteristics of the imaging optical system 6 shown in FIG. 8 on the optical axis and at the maximum image height performed with an optical simulation software Code-V (trade name). In FIGS. 9 to 11, curves A and B represent the spatial frequency characteristics in the x- and y-axis directions, respectively, on the optical axis, and curves C and D represent the spatial frequency characteristics in the x- and y-axis directions, respectively, at the maximum image height. The x- and y-axis directions are set coincident with the coordinates of the pupil modulation element 7.

FIG. 9 shows the spatial frequency response of the optical system 6 in a case where the distance to a subject is 100 millimeters. Phase components in this case are shown in Table 1 below.

FIG. 10 shows the spatial frequency response of the optical system 6 in a case where the subject distance is 13.5 millimeters. Phase components in this case are shown in Table 2 below.

FIG. 11 shows the spatial frequency response of the optical system 6 in a case where the subject distance is 5 millimeters. Phase components in this case are shown in Table 3 below.

TABLE 1

| Spatial frequency (L/MM) | Phase shift (deg) | | | |
| --- | --- | --- | --- | --- |
| | On optical axis | | At maximum image height | |
| | X-axis direction | X-axis direction | X-axis direction | X-axis direction |
| 0 | 0 | 0 | 0 | 0 |
| 5 | 55 | −55 | 53 | −51 |
| 10 | 45 | −43 | 51 | −54 |
| 15 | 51 | −52 | 46 | −49 |
| 20 | 49 | −48 | 53 | −57 |
| 25 | 54 | −54 | 53 | −60 |
| 30 | 50 | −50 | 56 | −65 |
| 35 | 54 | −53 | 61 | −71 |
| 40 | 58 | −57 | 68 | −79 |
| 45 | 62 | −61 | 70 | −83 |
| 50 | 66 | −65 | 74 | −93 |
| 55 | 72 | −71 | 87 | −108 |
| 60 | 79 | −78 | 91 | −111 |
| 65 | 86 | −85 | 103 | −133 |
| 70 | 98 | −97 | 113 | −141 |
| 75 | 106 | −105 | 126 | −163 |
| 80 | 121 | −120 | 141 | −179 |
| 85 | 132 | −132 | 159 | 157 |
| 90 | 151 | −150 | 175 | 134 |
| 95 | 166 | −165 | −162 | 111 |
| 100 | −171 | 172 | −140 | 82 |

TABLE 2

| Spatial frequency (L/MM) | Phase shift (deg) | | | |
| --- | --- | --- | --- | --- |
| | On optical axis | | At maximum image height | |
| | X-axis direction | X-axis direction | X-axis direction | X-axis direction |
| 0 | 0 | 0 | 0 | 0 |
| 5 | 50 | −50 | 50 | −50 |
| 10 | 49 | −47 | 51 | −53 |
| 15 | 42 | −39 | 44 | −48 |
| 20 | 51 | −49 | 52 | −56 |
| 25 | 48 | −46 | 50 | −59 |
| 30 | 53 | −51 | 54 | −65 |
| 35 | 56 | −54 | 57 | −71 |
| 40 | 58 | −57 | 61 | −75 |
| 45 | 64 | −62 | 69 | −80 |
| 50 | 69 | −68 | 73 | −96 |
| 55 | 75 | −74 | 77 | −104 |
| 60 | 82 | −81 | 92 | −113 |
| 65 | 91 | −89 | 97 | −131 |
| 70 | 102 | −101 | 112 | −141 |
| 75 | 112 | −111 | 124 | −162 |

TABLE 2-continued

| Spatial frequency (L/MM) | Phase shift (deg) | | | |
|---|---|---|---|---|
| | On optical axis | | At maximum image height | |
| | X-axis direction | X-axis direction | X-axis direction | X-axis direction |
| 80 | 126 | −125 | 139 | −178 |
| 85 | 140 | −139 | 155 | 158 |
| 90 | 157 | −156 | 174 | 137 |
| 95 | 174 | −173 | −164 | 110 |
| 100 | −162 | 163 | −143 | 84 |

TABLE 3

| Spatial frequency (L/MM) | Phase shift (deg) | | | |
|---|---|---|---|---|
| | On optical axis | | At maximum image height | |
| | X-axis direction | X-axis direction | X-axis direction | X-axis direction |
| 0 | 0 | 0 | 0 | 0 |
| 5 | 38 | −41 | 44 | −48 |
| 10 | 46 | −46 | 50 | −53 |
| 15 | 35 | −33 | 38 | −46 |
| 20 | 35 | −35 | 46 | −54 |
| 25 | 38 | −36 | 44 | −57 |
| 30 | 36 | −35 | 49 | −63 |
| 35 | 36 | −36 | 53 | −68 |
| 40 | 38 | −38 | 55 | −74 |
| 45 | 41 | −41 | 58 | −80 |
| 50 | 44 | −43 | 65 | −94 |
| 55 | 50 | −49 | 74 | −101 |
| 60 | 54 | −53 | 78 | −112 |
| 65 | 63 | −61 | 91 | −128 |
| 70 | 68 | −67 | 101 | −141 |
| 75 | 80 | −79 | 113 | −159 |
| 80 | 89 | −88 | 130 | −178 |
| 85 | 103 | −103 | 143 | 161 |
| 90 | 116 | −115 | 161 | 138 |
| 95 | 135 | −134 | −177 | 113 |
| 100 | 151 | −150 | −156 | 88 |

It will be understood from FIGS. 9 to 11 that the spatial frequency characteristics of the optical system 6 are approximately constant irrespective of the distance to the subject. When the solid-state image pickup device 5 has a pixel pitch of 7 micrometers, the Nyquist frequency of the solid-state image pickup device 5 is 71 line pairs per millimeter. As will be understood from the diagrams, the spatial frequency response is not zero at 71 line pairs per millimeter or lower. Therefore, the spatial frequency characteristics can be restored by a spatial frequency characteristic restoring device. Accordingly, a high-resolution image can be produced by the same spatial frequency characteristic restoring device independently of the distance to the subject.

Figure 12:
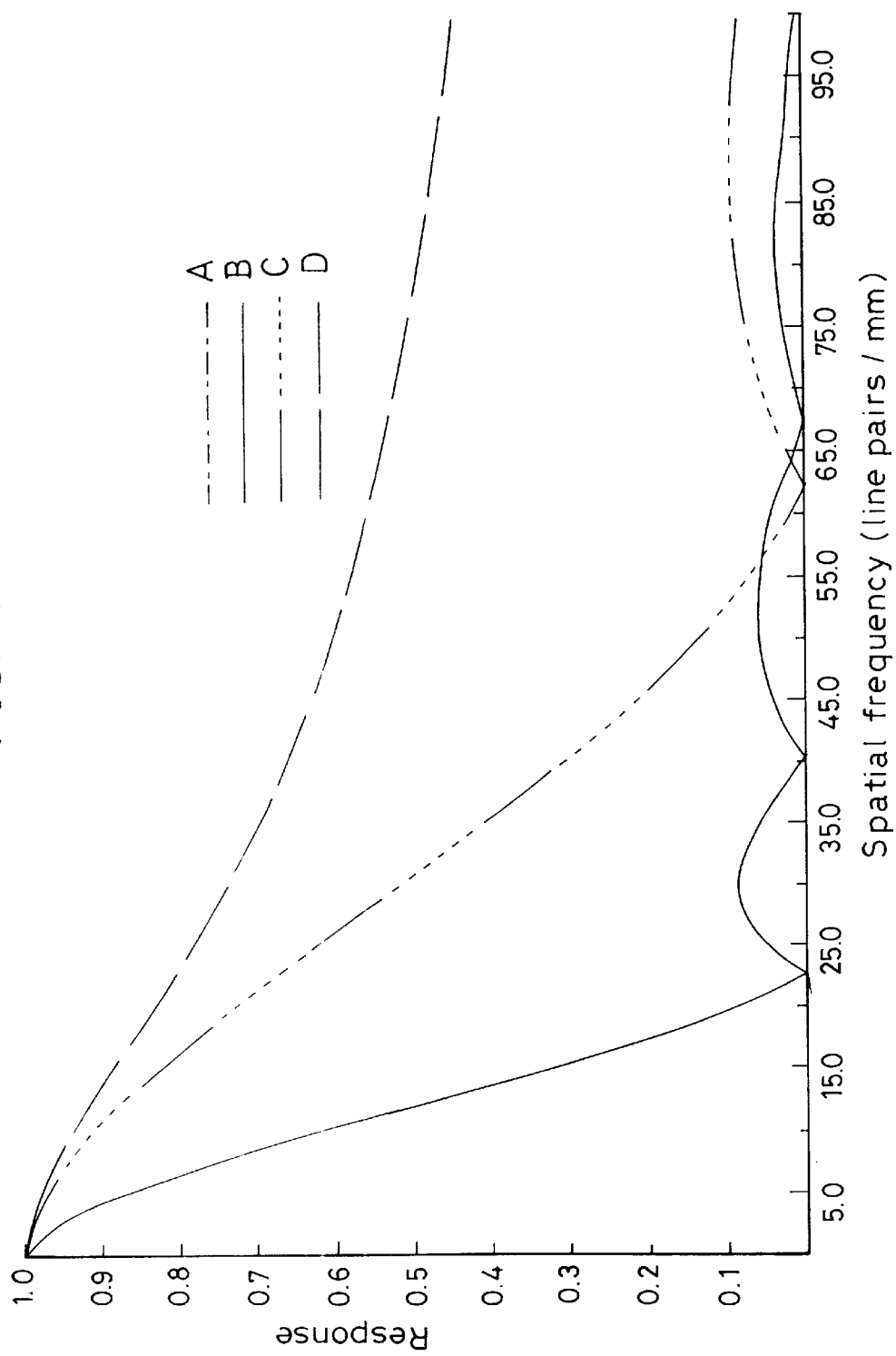
FIG. 12 is a diagram corresponding to FIG. 9, showing the spatial frequency response of an imaging optical system according to a comparative example with respect to the example shown in FIG. 8.
Figure 13:
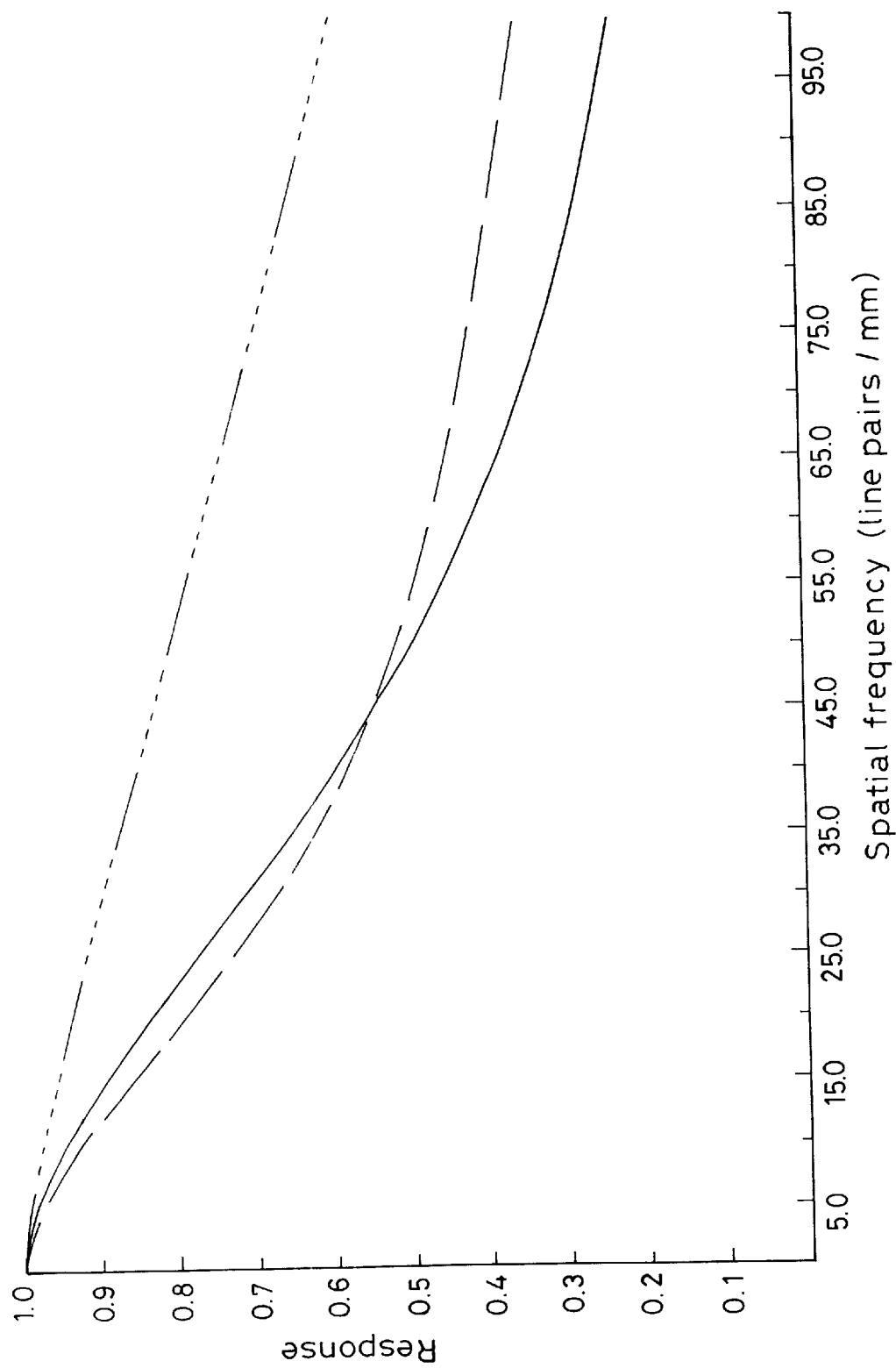
FIG. 13 is a diagram corresponding to FIG. 10, showing the spatial frequency response of the imaging optical system according to the comparative example with respect to the example shown in FIG. 8.
Figure 14:
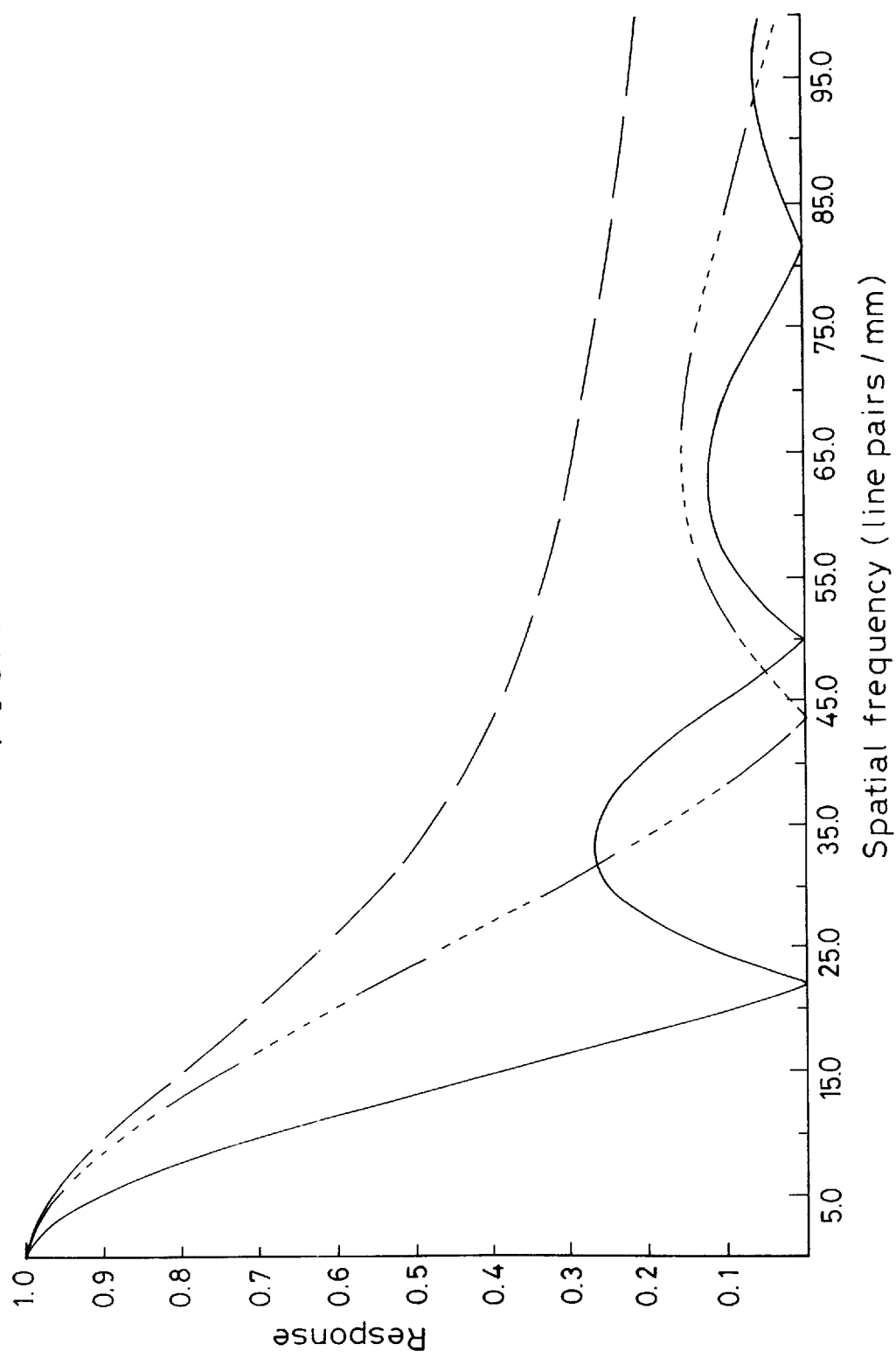
FIG. 14 is a diagram corresponding to FIG. 11, showing the spatial frequency response of the imaging optical system according to the comparative example with respect to the example shown in FIG. 8.

FIGS. 12 to 14 show the response of a conventional imaging optical system that does not use the pupil modulation element 7 in FIG. 8, as a comparative example. FIG. 12 shows the response in a case where the subject distance is 100 millimeters. FIG. 13 shows the response in a case where the subject distance is 13.5 millimeters. FIG. 14 shows the response in a case where the subject distance is 5 millimeters. Curves A to D in FIGS. 12 to 14 are the same as those in FIGS. 9 to 11. It will be understood from FIGS. 12 to 14 that the spatial frequency characteristics of the optical system change with the subject distance. Accordingly, it is impossible to produce a high-resolution image with the same spatial frequency characteristic restoring device irrespective of the subject distance. At the subject distance of 100 millimeters and 5 millimeters, the spatial frequency characteristics of the optical system are degraded. Therefore, the depth of field is practically smaller than the region of from 100 millimeters to 5 millimeters.

Thus, according to the example of the present invention, a high-resolution image can be produced in the subject distance range of the order of from 5 millimeters to 100 millimeters by a combination of a pupil modulation element and a spatial frequency characteristic restoring device. Thus, the depth of field is favorably enlarged.

In this example, there are differences between the spatial frequency characteristics on the optical axis and those at the maximum image height due to the difference in the angle of incidence of light rays on the pupil modulation element 7. Accordingly, the deviation of the spatial frequency characteristics at each image height can be minimized by designing the optical system 6 so that the angle of incidence of light rays on the pupil modulation element 7 is reduced. Consequently, an image having even higher quality throughout it can be produced by the spatial frequency characteristic restoring device.

Incidentally, the pupil modulation element 7 in this example is arranged such that the amounts of conversion of the spatial frequency characteristics in the x- and y-axis directions are the same. However, the pupil modulation element 7 may be arranged such that the amounts of conversion in the x- and y-axis directions are different from each other. For example, the aperture configuration of the aperture stop may be a rectangular shape. The pupil modulation element 7 may use a free-form surface configuration having coefficients different in the x- and y-axis directions.

In the monitor 4 for observing the subject image, the horizontal resolution and the vertical resolution are generally different from each other. When the horizontal direction of the monitor 4 and the x-axis direction of the pupil modulation element 7 correspond to each other, and so do the vertical direction of the monitor 4 and the y-axis direction of the pupil modulation element 7, the system may be arranged to optimize the amounts of conversion in the x- and y-axis directions and the amounts of restoration performed by the spatial frequency characteristic restoring device.

Figure 15:
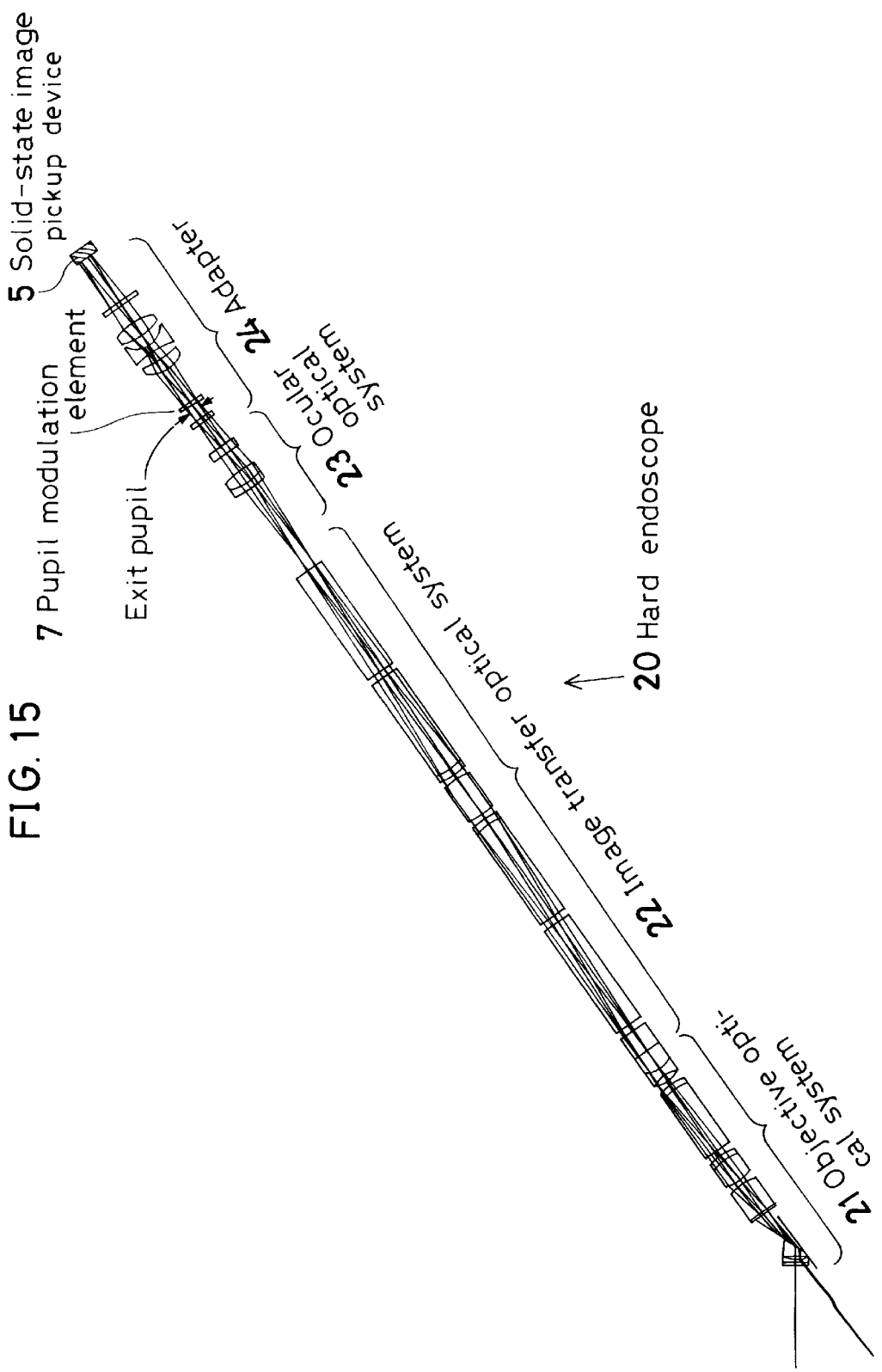
FIG. 15 is a sectional view of another example of an imaging optical system.

FIG. 15 shows another example of an imaging optical system. FIG. 15 is a sectional view of an imaging optical system of an endoscope system including a hard endoscope 20 having an objective optical system 21 that forms a subject image. The hard endoscope 20 further has an image transfer optical system 22 and an ocular optical system 23. An adapter 24 forms the subject image sent from the hard endoscope 20 on a solid-state image pickup device 5. In this example, the hard endoscope 20 and the adapter 24 are detachable from each other, so that different types of hard endoscope 20 and adapter 24 can be connected to each other.

A pupil modulation element 7 is placed at the pupil position of an optical system of the adapter 24. The position of the exit pupil of the hard endoscope 20 is coincident with the position of the pupil modulation element 7.

The pupil modulation element 7 uses a free-form surface having a configuration expressed by $0.001(x^3+y^3)$. The refractive index of the pupil modulation element 7 is 1.52. It should be noted that the optical axis of the optical system is defined as a z-axis, and coordinate axes perpendicularly intersecting the z-axis are defined as x- and y-axes, respectively. Lengths are given in millimeters. The radius of the exit pupil of the hard endoscope 20 is 2.3 millimeters.

In this case, the pupil modulation element 7 performs phase modulation of $\exp\{i21\pi(x^3+y^3)/2.3^3\}$ on parallel rays of light of wavelength 587.6 nanometers.

Figure 16:
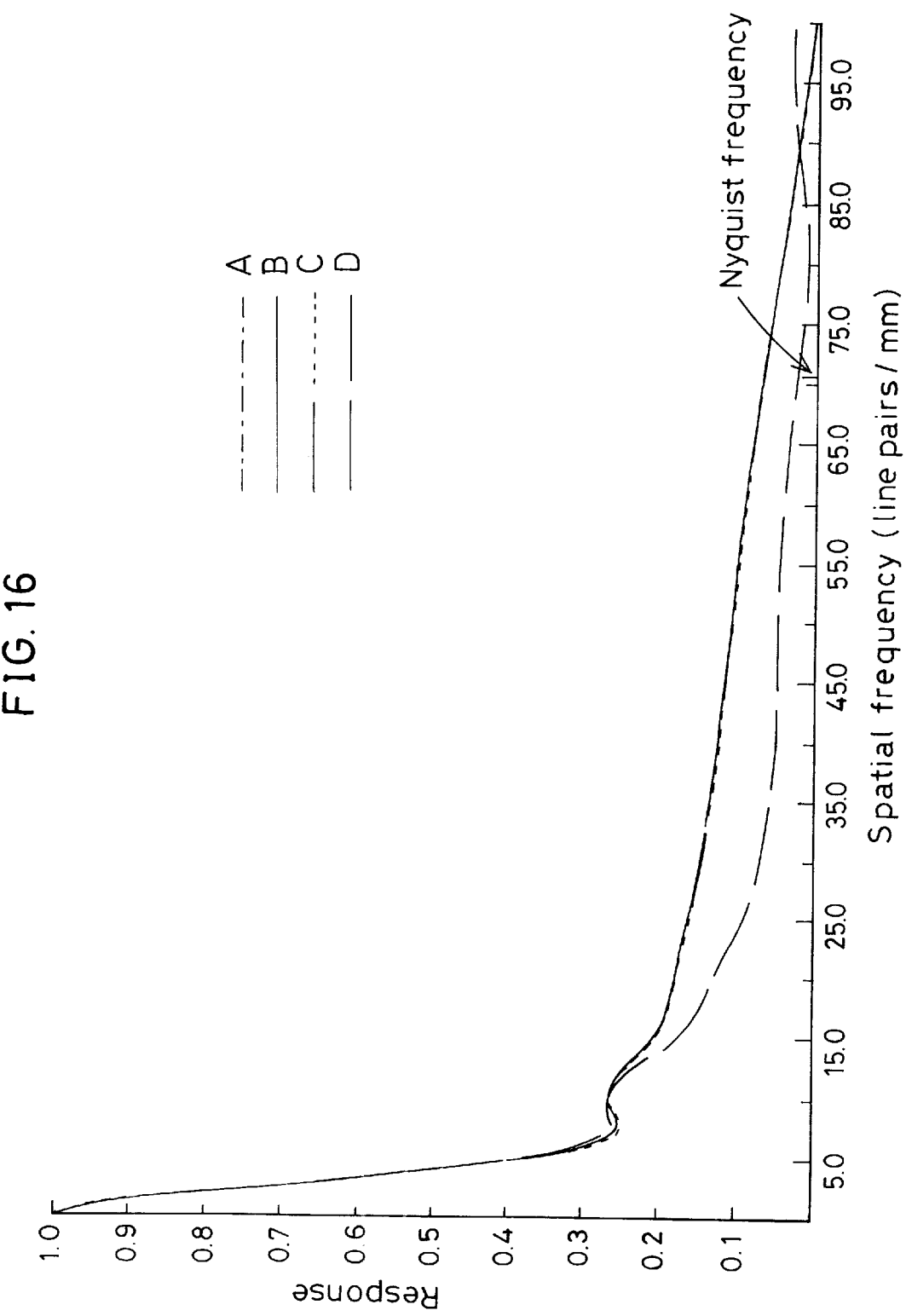
FIG. 16 is a diagram showing the spatial frequency response of the imaging optical system shown in FIG. 15 in a case where the subject distance is 150 millimeters.
Figure 17:
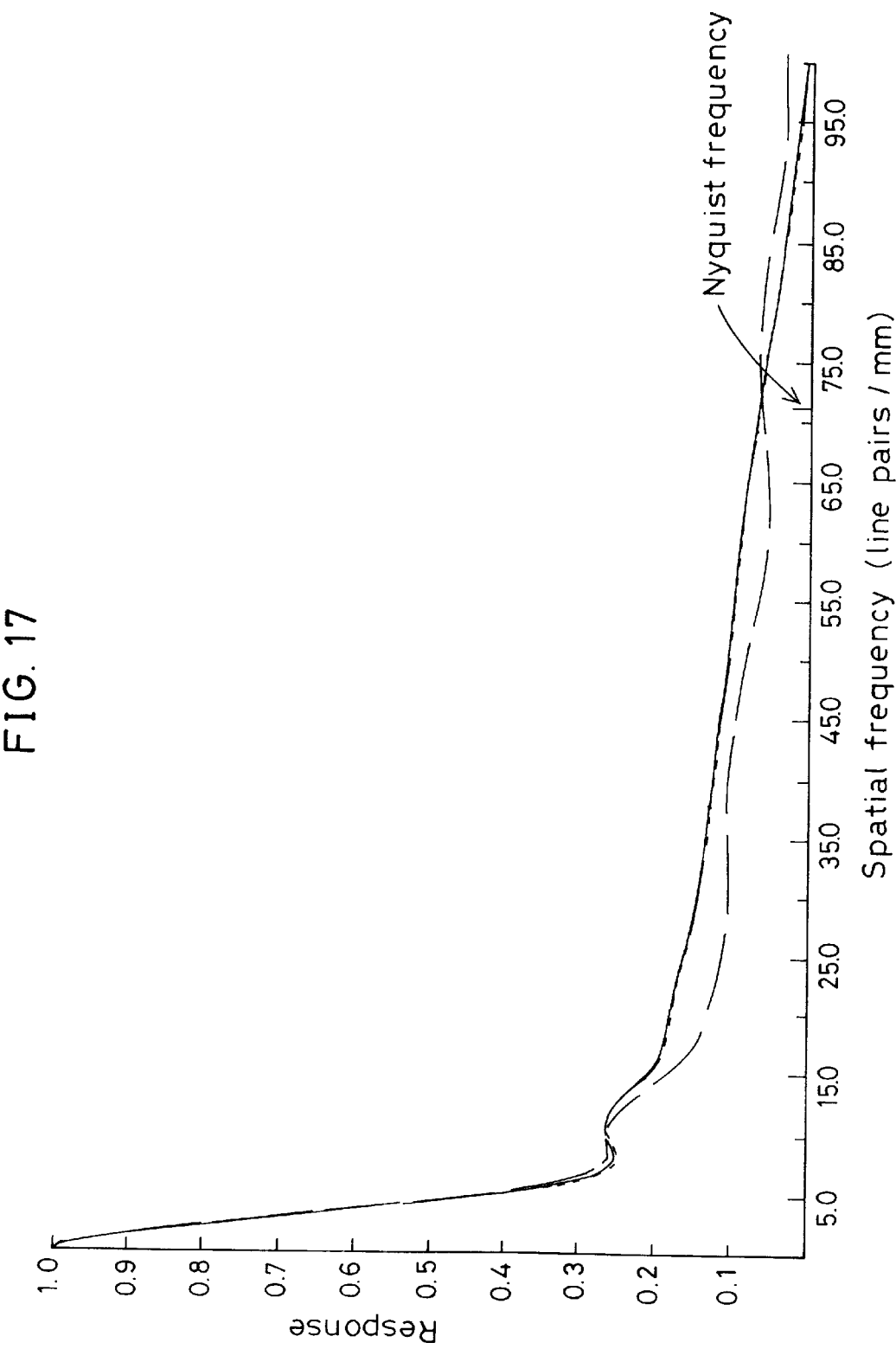
FIG. 17 is a diagram showing the spatial frequency response of the imaging optical system shown in FIG. 15 in a case where the subject distance is 65 millimeters.
Figure 18:
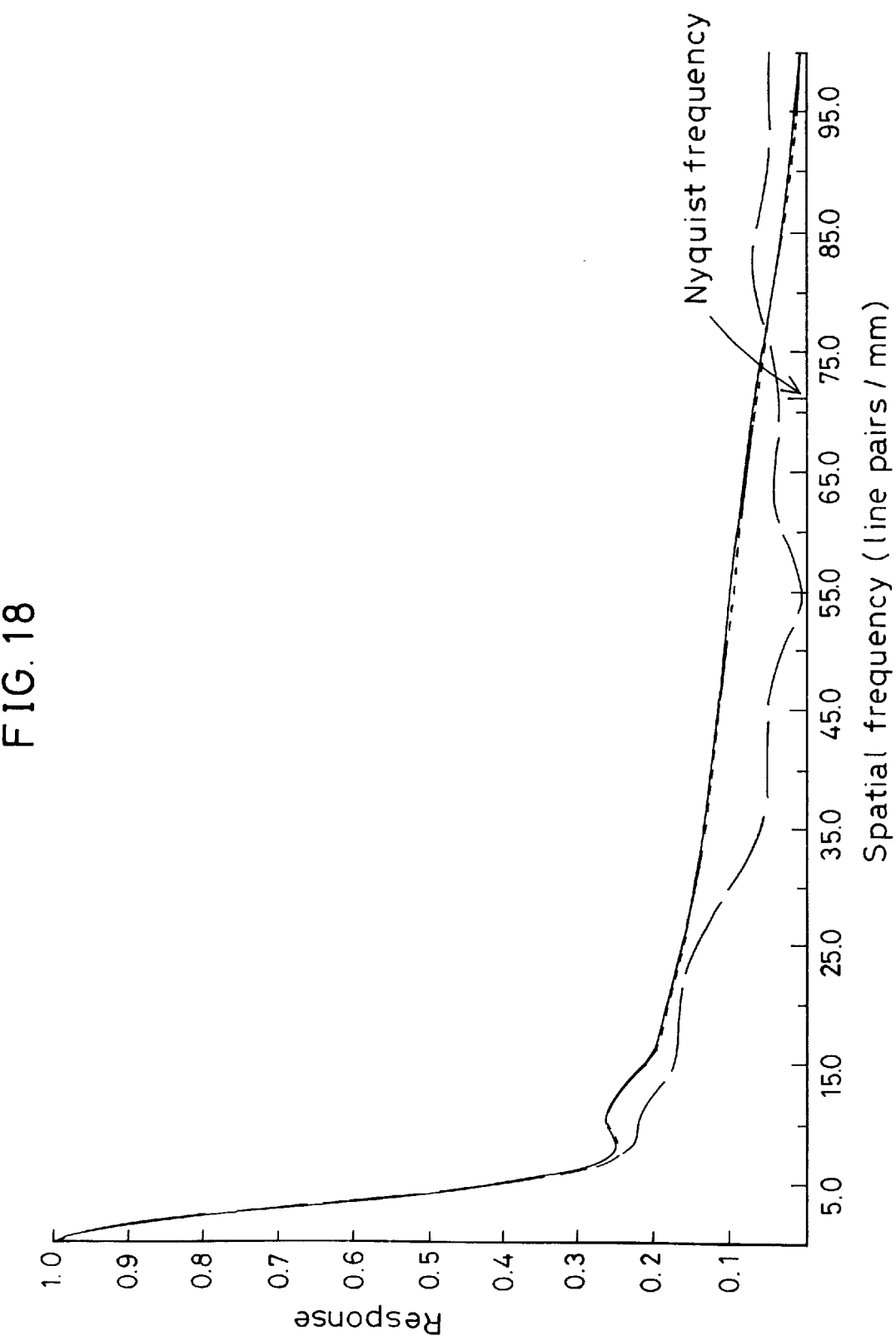
FIG. 18 is a diagram showing the spatial frequency response of the imaging optical system shown in FIG. 15 in a case where the subject distance is 30 millimeters.

FIGS. 16 to 18 show the results of calculation of the spatial frequency characteristics of the imaging optical system shown in FIG. 15 on the optical axis and at the maximum image height performed with an optical simulation software Code-V (trade name). Curves A and D in FIGS. 16 to 18 are the same as those in FIGS. 9 to 11.

FIG. 16 shows the spatial frequency response of the above-described optical system in a case where the distance to a subject is 150 millimeters. Phase components in this case are shown in Table 4 below.

FIG. 17 shows the spatial frequency response of the above-described optical system in a case where the subject distance is 65 millimeters. Phase components in this case are shown in Table 5 below.

FIG. 18 shows the spatial frequency response of the above-described optical system in a case where the subject distance is 30 millimeters. Phase components in this case are shown in Table 6 below.

TABLE 4

| Spatial frequency (L/MM) | Phase shift (deg) | | | |
|---|---|---|---|---|
| | On optical axis | | At maximum image height | |
| | X-axis direction | X-axis direction | X-axis direction | X-axis direction |
| 0 | 0 | 0 | 0 | 0 |
| 5 | 41 | −40 | 41 | −47 |
| 10 | 45 | −44 | 45 | −55 |
| 15 | 45 | −44 | 46 | −65 |
| 20 | 48 | −47 | 48 | −78 |
| 25 | 51 | −50 | 52 | −95 |
| 30 | 57 | −56 | 58 | −121 |
| 35 | 66 | −65 | 66 | −153 |
| 40 | 77 | −76 | 78 | 173 |
| 45 | 91 | −90 | 93 | 141 |
| 50 | 198 | −107 | 111 | 109 |
| 55 | 130 | −129 | 133 | 73 |
| 60 | 156 | −155 | 160 | 37 |
| 65 | −172 | 173 | −166 | −1 |
| 70 | −137 | 138 | −128 | −49 |
| 75 | −96 | 97 | −84 | −109 |
| 80 | −50 | 51 | −36 | 162 |
| 85 | 0 | 0 | 16 | 69 |
| 90 | 58 | −57 | 75 | −3 |
| 95 | 120 | −119 | 142 | −74 |
| 100 | −170 | 171 | −126 | −153 |

TABLE 5

| Spatial frequency (L/MM) | Phase shift (deg) | | | |
|---|---|---|---|---|
| | On optical axis | | At maximum image height | |
| | X-axis direction | X-axis direction | X-axis direction | X-axis direction |
| 0 | 0 | 0 | 0 | 0 |
| 5 | 41 | −40 | 41 | −40 |
| 10 | 45 | −44 | 45 | −40 |
| 15 | 45 | −44 | 46 | −46 |
| 20 | 47 | −46 | 48 | −55 |
| 25 | 51 | −50 | 52 | −74 |
| 30 | 57 | −56 | 58 | −90 |
| 35 | 66 | −65 | 66 | −105 |
| 40 | 77 | −76 | 78 | −119 |
| 45 | 91 | −90 | 92 | −133 |
| 50 | 108 | −107 | 111 | −151 |
| 55 | 130 | −129 | 133 | −178 |
| 60 | 156 | −155 | 160 | 144 |
| 65 | −173 | 174 | −167 | 99 |
| 70 | −137 | 138 | −129 | 55 |
| 75 | −97 | 98 | −86 | 14 |
| 80 | −51 | 52 | −37 | −28 |
| 85 | 0 | 0 | 15 | −78 |
| 90 | 57 | −56 | 75 | −142 |
| 95 | 119 | −118 | 144 | 136 |
| 100 | −171 | 172 | −116 | 47 |

TABLE 6

| Spatial frequency (L/MM) | Phase shift (deg) | | | |
|---|---|---|---|---|
| | On optical axis | | At maximum image height | |
| | X-axis direction | X-axis direction | X-axis direction | X-axis direction |
| 0 | 0 | 0 | 0 | 0 |
| 5 | 41 | −40 | 41 | −27 |
| 10 | 44 | −43 | 44 | −21 |
| 15 | 45 | −44 | 45 | −22 |
| 20 | 47 | −46 | 47 | −19 |
| 25 | 51 | −50 | 51 | −6 |
| 30 | 57 | −56 | 56 | 3 |
| 35 | 65 | −64 | 65 | −4 |
| 40 | 77 | −76 | 76 | −28 |
| 45 | 90 | −89 | 90 | −35 |
| 50 | 108 | −107 | 109 | −32 |
| 55 | 129 | −128 | 130 | −129 |
| 60 | 155 | −154 | 157 | −174 |
| 65 | −174 | 175 | −169 | 174 |
| 70 | −138 | 139 | −132 | 139 |
| 75 | −97 | 98 | −90 | 85 |
| 80 | −51 | 52 | −42 | 50 |
| 85 | 0 | 0 | 12 | 17 |
| 90 | 57 | −56 | 76 | −33 |
| 95 | 118 | −117 | 154 | −104 |
| 100 | −173 | 174 | −109 | −164 |

It will be understood from FIGS. 16 to 18 that the pupil modulation element 7 enables the spatial frequency characteristics of the optical system to be approximately constant irrespective of the distance to the subject. When the solid-state image pickup device 5 has a pixel pitch of 7 micrometers, the Nyquist frequency of the solid-state image pickup device 5 is 71 line pairs per millimeter. As will be understood from the diagrams, the spatial frequency response is not zero at 71 line pairs per millimeter or lower. Therefore, the spatial frequency characteristics can be restored by a spatial frequency characteristic restoring device. Accordingly, a high-resolution image can be produced by the same spatial frequency characteristic restoring device independently of the distance to the subject. It is possible to ensure a depth of field of the order of from 30 millimeters to 150 millimeters.

Figure 19:
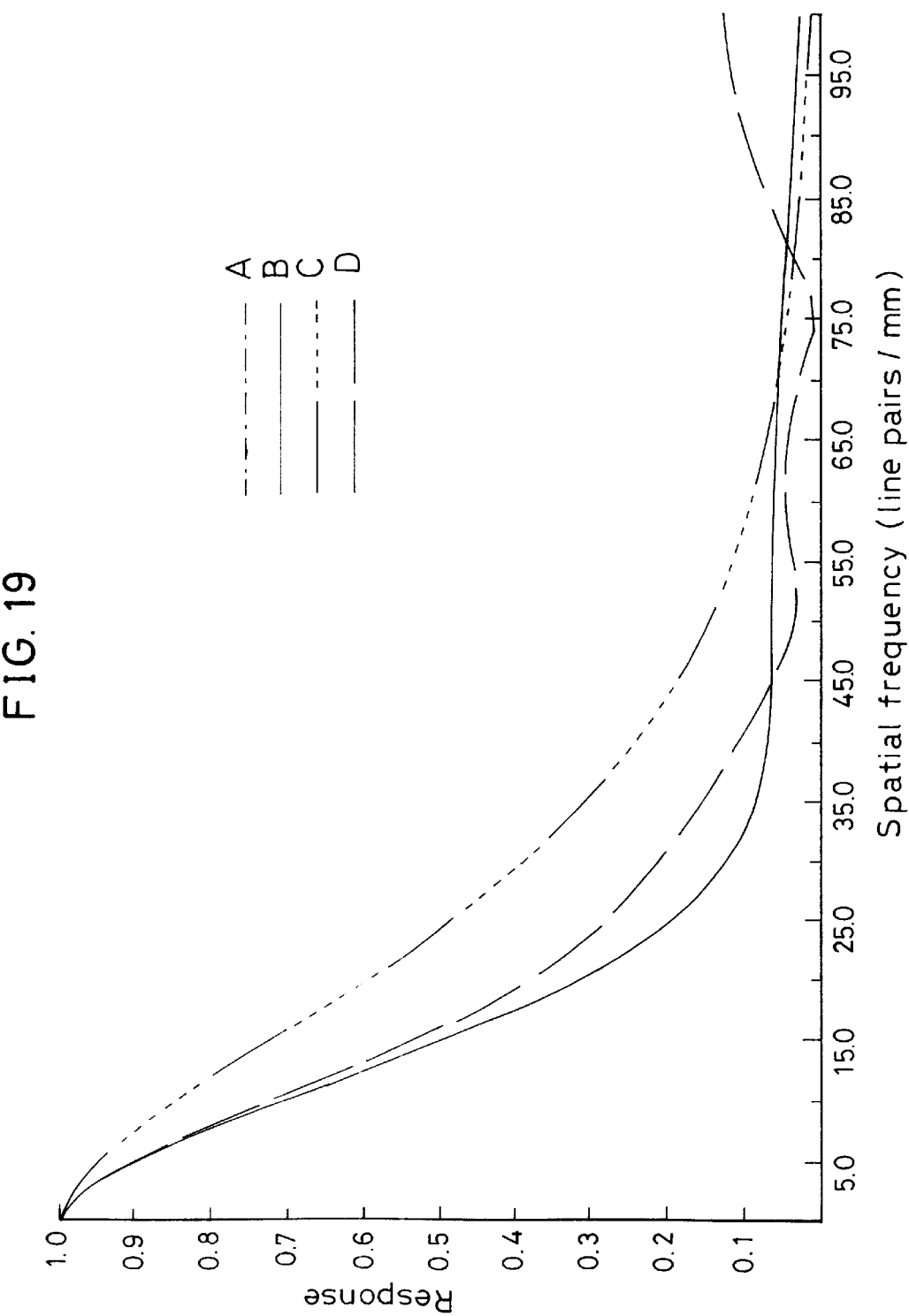
FIG. 19 is a diagram corresponding to FIG. 16, showing the spatial frequency response of an imaging optical system according to a comparative example with respect to the example shown in FIG. 15.
Figure 20:
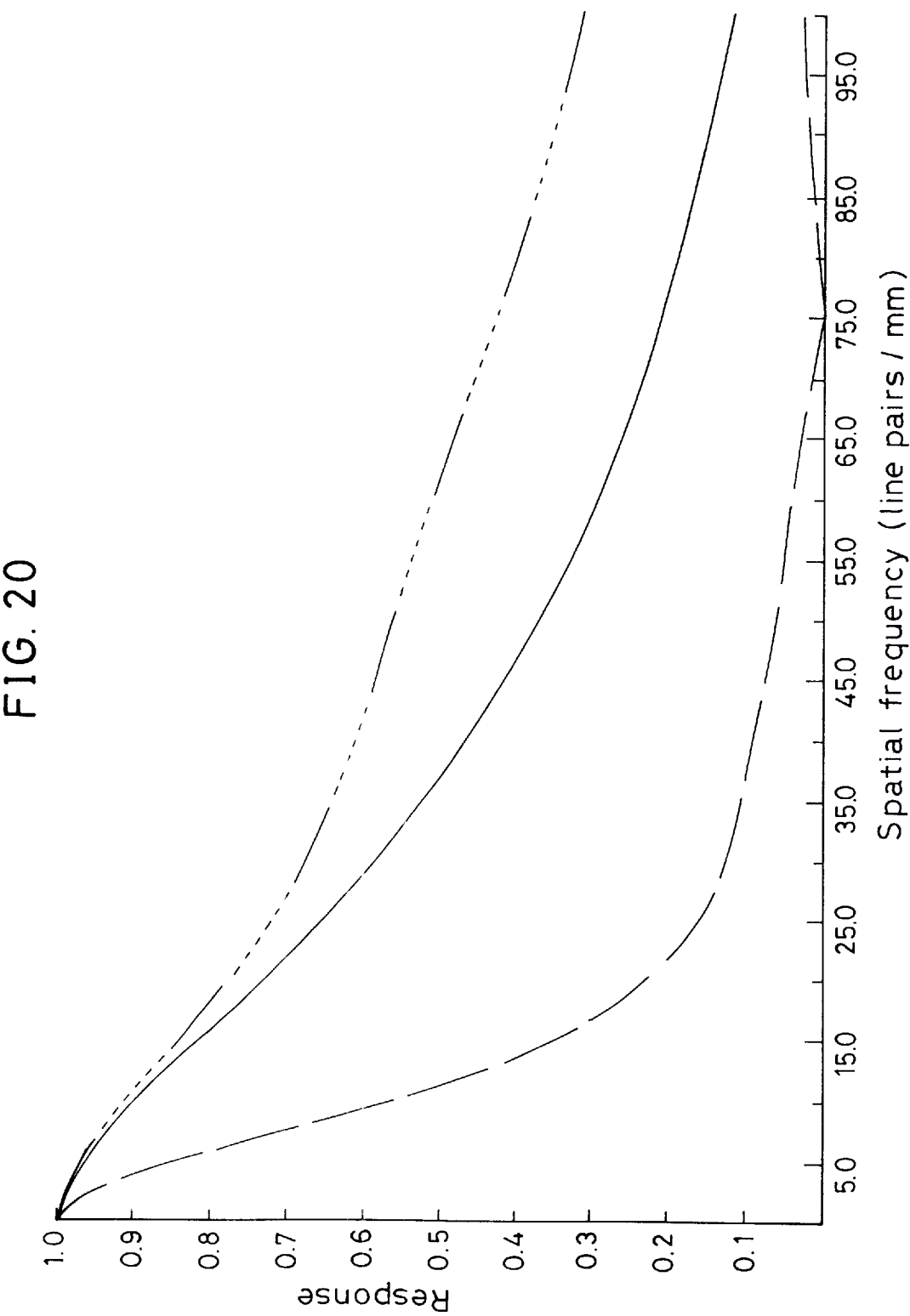
FIG. 20 is a diagram corresponding to FIG. 17, showing the spatial frequency response of the imaging optical system according to the comparative example with respect to the example shown in FIG. 15.
Figure 21:
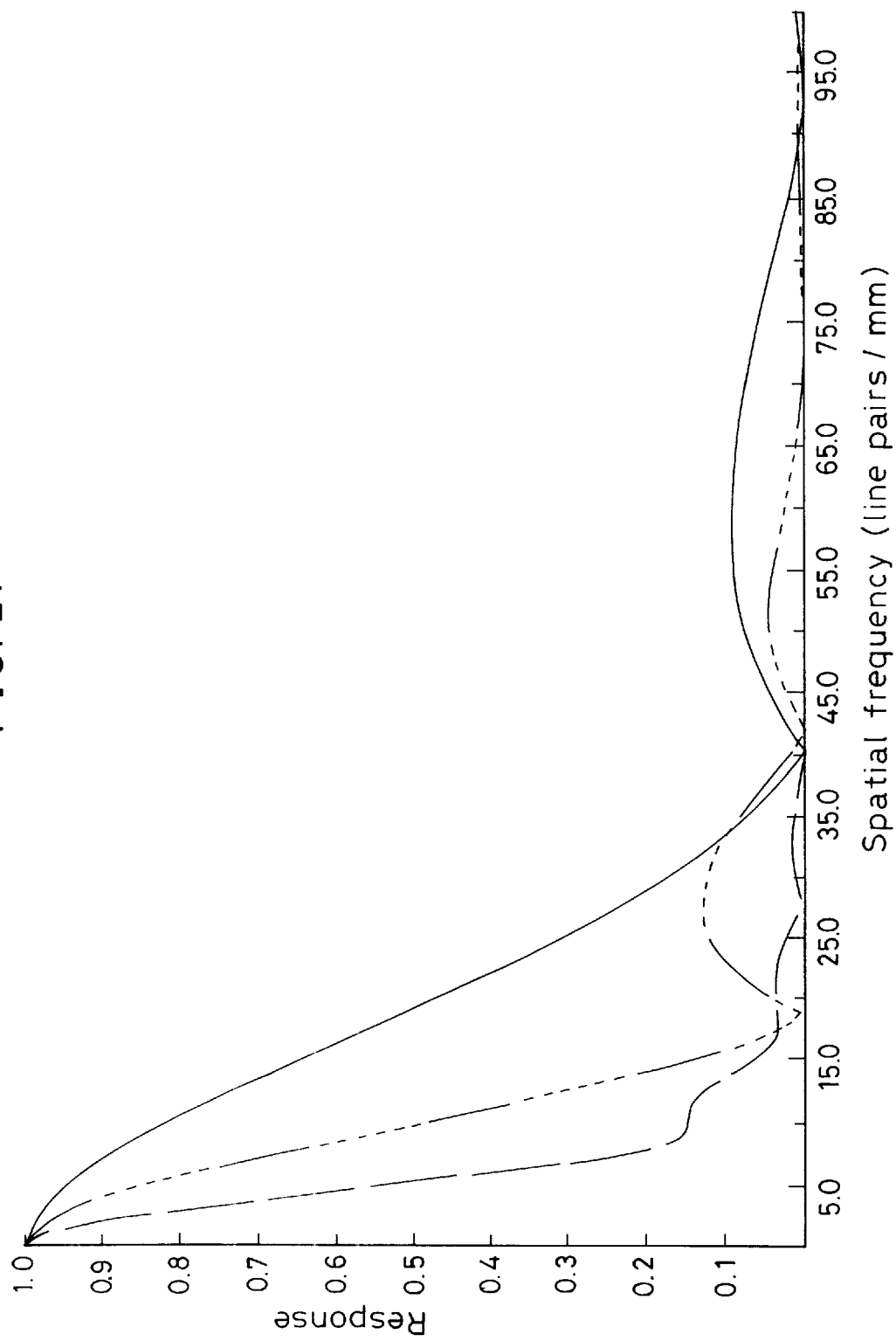
FIG. 21 is a diagram corresponding to FIG. 18, showing the spatial frequency response of the imaging optical system according to the comparative example with respect to the example shown in FIG. 15.

FIGS. 19 to 21 show the response of an imaging optical system arranged as shown in FIG. 15 except that it does not use the pupil modulation element 7, as a comparative example. FIG. 19 shows the response in a case where the subject distance is 150 millimeters. FIG. 20 shows the response in a case where the subject distance is 65 millimeters. FIG. 21 shows the response in a case where the subject distance is 30 millimeters. Curves A to D in FIGS. 19 to 21 are the same as those in FIGS. 9 to 11. It will be understood from FIGS. 19 to 21 that the spatial frequency characteristics of the optical system change with the subject distance. Accordingly, it is impossible to produce a high-resolution image with the same spatial frequency characteristic restoring device irrespective of the subject distance. At the subject distance of 150 millimeters and 30 millimeters, the spatial frequency characteristics of the optical system are degraded. Therefore, the depth of field is practically smaller than the region of from 150 millimeters to 30 millimeters.

Thus, according to the example of the present invention, a high-resolution image can be produced in the subject distance range of from about 150 millimeters to about 30 millimeters by a combination of a pupil modulation element and a spatial frequency characteristic restoring device. Thus, the depth of field is favorably enlarged.

In addition, because the pupil modulation element 7 is placed in the adapter 24, the hard endoscope 20 can also be used with an eyepiece as in the conventional endoscope systems. The endoscope system can also be used as a conventional system by replacing the adapter 24 with a conventional adapter having no spatial frequency characteristic converting device.

Hard endoscopes 20 of different types can be selectively connected to the adapter 24. The amount of modulation effected by the pupil modulation element 7 depends on the type of hard endoscope 20 connected because of the difference in the exit pupil diameter. For example, when the pupil modulation element 7 has a free-form surface with a configuration expressed by $0.001(x^3+y^3)$ and a hard endoscope 20 having an exit pupil radius R (millimeter) is connected to the adapter 24, the amount of modulation effected by the pupil modulation element 7 is given by $$\exp\{0.001(x^3+y^3)(n-1)2\pi/\lambda\}$$

In the above-described expression, $|x|<R$ and $|y|<R$. Symbol n is the refractive index of the pupil modulation element 7, and $\lambda$ (mm) is the wavelength of the light rays. In addition, x and y are expressed in millimeters.

That is, when a hard endoscope 20 having a small exit pupil radius is connected, the amount of modulation effected by the pupil modulation element 7 is small.

Accordingly, the depth of field of each of different types of hard endoscopes 20 can be enlarged with a single pupil modulation element 7 by using a spatial frequency characteristic restoring device corresponding to the amount of modulation effected by the pupil modulation element 7, which depends on the pupil diameter. This enables a reduction in the number of pupil modulation elements 7 required for the endoscope system. Accordingly, it becomes possible to reduce the cost.

In this example, there are differences between the spatial frequency characteristics on the optical axis and those at the maximum image height due to the difference in the angle of incidence of light rays on the pupil modulation element 7 and also due to the difference between the axial and extra-axial exit pupil diameters of the hard endoscope 20. Accordingly, the deviation of the spatial frequency characteristics at each image height can be minimized, for example, by designing the optical system so that the angle of incidence of light rays on the pupil modulation element 7 is reduced, or designing the system so that the axial exit pupil diameter of the hard endoscope 20 and the extra-axial exit pupil diameter thereof are equal to each other. Consequently, it is possible to produce an image having even higher quality throughout it.

As will be clear from the foregoing description, the endoscope system according to the present invention has a spatial frequency characteristic restoring device corresponding to the spatial frequency characteristics of an endoscope connected thereto. Therefore, it is possible to enlarge the depth of field and to produce an image of high resolution for any type of endoscope irrespective of whether or not the connected endoscope has a spatial frequency characteristic converting device and regardless of the type of spatial frequency characteristic converting device.

What is claimed is:

1. An endoscope system comprising:
a plurality of different types of endoscopes, at least one of said plurality of different types of endoscopes having a spatial frequency characteristic converter in an optical system thereof to convert spatial frequency characteristics of said optical system;
a camera controller to which one of said plurality of different types of endoscopes is selectively connected;
a monitor for displaying a signal from said camera controller; and
a spatial frequency characteristic restoring device selectively operable to restore the spatial frequency characteristics converted by said spatial frequency characteristic converter.

2. An endoscope system according to claim 1, wherein said spatial frequency characteristic converter performs conversion such that the spatial frequency characteristics of said optical system are approximately constant irrespective of a distance to a subject over a wider depth of field than a depth of field of said optical system when said spatial frequency characteristic converter is removed.

3. An endoscope system according to claim 1, wherein when one of said at least one endoscope having said spatial frequency characteristic converter is connected to said camera controller, said spatial frequency characteristic restoring device is used, whereas when an endoscope that does not have said spatial frequency characteristic converter is connected to said camera controller, said spatial frequency characteristic restoring device is not used.

4. An endoscope system according to claim 1, wherein said spatial frequency characteristic restoring device restores the spatial frequency characteristics converted by said spatial frequency characteristic converter on a basis of measured values of spatial frequency characteristics of an optical system of an endoscope connected to said camera controller.

5. An endoscope system according to claim 1, wherein said spatial frequency characteristic restoring device is provided in said camera controller.

6. An endoscope system according to claim 1, wherein said spatial frequency characteristic restoring device is provided in an endoscope having said spatial frequency characteristic converter.

7. An endoscope system according to claim 1, wherein said spatial frequency characteristic converter is a pupil modulation element.

8. An endoscope system according to claim 1, wherein at least one of said plurality of different types of endoscopes has an objective optical system for forming a subject image and a solid-state image pickup device for detecting the image formed by said objective optical system.

9. An endoscope system according to claim 1, wherein at least one of said plurality of different types of endoscopes is a hard endoscope including an objective optical system for forming a subject image, an image transfer optical system, and an ocular optical system, said endoscope system having an adapter for forming the subject image from said hard endoscope on a solid-state image pickup device.

10. An endoscope system according to claim 9, wherein said spatial frequency characteristic converter is provided in said adapter.

11. An endoscope system according to claim 10, wherein said spatial frequency characteristic restoring device restores the spatial frequency characteristics converted by said spatial frequency characteristic converter according to an exit pupil diameter of said hard endoscope.

12. An endoscope system according to claim 1, wherein at least one of said plurality of different types of endoscopes has an optical system whose spatial frequency characteristics are variable, and said spatial frequency characteristic restoring device restores the spatial frequency characteristics converted by said spatial frequency characteristic converter according to a change in the spatial frequency characteristics of said optical system.

13. An endoscope system according to claim 12, wherein said optical system is a variable-focus optical system.

14. An endoscope system according to claim 13, wherein said spatial frequency characteristic restoring device restores said spatial frequency characteristics converted by said spatial frequency characteristic converter according to a change in a focal length of said optical system.

* * * * *